(12) United States Patent
Kriger

(10) Patent No.: US 10,295,399 B2
(45) Date of Patent: May 21, 2019

(54) GLOBAL OVERWEIGHT AND OBESITY PREVENTING AND TRACKING SYSTEM AND METHOD

(76) Inventor: Yefim G. Kriger, Ansonia, CT (US)

(*) Notice: Subject to any disclaimer, the term of this patent is extended or adjusted under 35 U.S.C. 154(b) by 1244 days.

(21) Appl. No.: 12/125,902

(22) Filed: May 22, 2008

(65) Prior Publication Data

US 2008/0294370 A1 Nov. 27, 2008

Related U.S. Application Data

(60) Provisional application No. 60/939,810, filed on May 23, 2007.

(51) Int. Cl.
*A61B 5/00* (2006.01)
*G01G 19/414* (2006.01)
(Continued)

(52) U.S. Cl.
CPC ..... *G01G 19/4146* (2013.01); *G01G 23/3735* (2013.01); *G06F 19/3418* (2013.01); *G06F 19/3475* (2013.01); *G06F 19/3481* (2013.01)

(58) Field of Classification Search
CPC ..... A61B 5/7275; A61B 5/0002; A61B 5/107; A61B 5/1072; A61G 5/7271;
(Continued)

(56) References Cited

U.S. PATENT DOCUMENTS 5,763,837 A * 6/1998 Davignon .............. G01G 19/50
128/921
6,181,996 B1 * 1/2001 Chou ..................... B60K 37/00
340/439

(Continued)

OTHER PUBLICATIONS

Nyhol et al. "The Validity of Obesity Based on Self-reported Weight and Height: Implications for Population Studies" 2007.*
(Continued)

*Primary Examiner* — Niketa I Patel
*Assistant Examiner* — Shirley X Jian

(57) ABSTRACT

An obesity preventing and tracking system, the system comprising: at least one in-building overweight and obesity preventing module for collecting anthropometry information from a person at a fixed location in order to forecast and prevent development of an obesity condition; and/or at least one on-board vehicle overweight and obesity preventing module for collecting the anthropometry information from the person in a vehicle operable by the person in order to forecast and prevent development of an obesity condition and/or at least one entertainment overweight and obesity preventing module for collecting anthropometry information from said person while said person is a guest at an entertainment facility in order to forecast and prevent development of an obesity condition; and a communications network for linking at least one in-building overweight and obesity preventing module and at least one on-board vehicle overweight and obesity preventing module and at least one entertainment overweight and obesity preventing module to a trend obesity preventing service for predicting the development of an obesity condition of the person.

9 Claims, 23 Drawing Sheets

(51) Int. Cl.
*G01G 23/37* (2006.01)
*G06F 19/00* (2018.01)

(58) Field of Classification Search
CPC ......... G06F 19/10–19/12; G06F 19/30–19/36;
G06F 19/3431; G06F 19/3437; G06F
19/345; G01G 19/44; G01G 19/50; A47C
31/123; G01M 99/001; G06Q 50/22–24
USPC ........ 600/300, 301; 128/903–905, 920, 921;
705/2–5
See application file for complete search history.

(56) References Cited

U.S. PATENT DOCUMENTS

| | | | | |
|---|---|---|---|---|
| 6,322,504 | B1* | 11/2001 | Kirshner | 600/300 |
| 6,345,839 | B1* | 2/2002 | Kuboki | B60R 21/01516 280/735 |
| 6,425,862 | B1* | 7/2002 | Brown | 600/300 |
| 6,585,328 | B1* | 7/2003 | Oexman et al. | 700/117 |
| 6,816,807 | B2* | 11/2004 | Kriger | 702/173 |
| 7,134,715 | B1* | 11/2006 | Fristedt | B60N 2/002 177/144 |
| 7,194,301 | B2* | 3/2007 | Jenkins et al. | 607/2 |
| 7,330,784 | B2* | 2/2008 | Johnson | B60N 2/002 280/731 |
| 7,465,272 | B2* | 12/2008 | Kriger | 600/300 |
| 7,774,212 | B2* | 8/2010 | Huang | G06F 19/3418 705/2 |
| 7,803,111 | B2* | 9/2010 | Kriger | 600/300 |
| 7,910,840 | B2* | 3/2011 | Chai | A61B 5/107 128/921 |
| 8,388,532 | B2* | 3/2013 | Morgan | A61B 5/0002 600/300 |
| 2002/0062069 | A1* | 5/2002 | Mault | 600/300 |
| 2003/0130595 | A1* | 7/2003 | Mault | 600/567 |
| 2004/0148127 | A1* | 7/2004 | Kriger | G06F 19/3475 702/173 |
| 2005/0080462 | A1* | 4/2005 | Jenkins et al. | 607/58 |
| 2005/0101875 | A1* | 5/2005 | Semler | A61B 5/04085 600/509 |
| 2005/0194192 | A1* | 9/2005 | Kriger | G01G 19/4142 177/25.19 |
| 2007/0185391 | A1* | 8/2007 | Morgan | A61B 5/0002 600/301 |
| 2007/0244375 | A1* | 10/2007 | Jenkins | A61N 1/36085 600/301 |
| 2008/0046291 | A1* | 2/2008 | Huang | G06F 19/3418 705/3 |
| 2008/0183421 | A1* | 7/2008 | Chai | 702/173 |
| 2009/0132099 | A1* | 5/2009 | Kriger | 701/1 |
| 2009/0182204 | A1* | 7/2009 | Semler | A61B 5/04085 600/301 |
| 2011/0125680 | A1* | 5/2011 | Bosworth et al. | 706/12 |
| 2011/0183870 | A1* | 7/2011 | Pan | C12Q 1/6883 506/17 |
| 2013/0011819 | A1* | 1/2013 | Horseman | A61B 5/6887 434/257 |
| 2013/0012786 | A1* | 1/2013 | Horseman | G06F 19/3418 600/301 |
| 2013/0012790 | A1* | 1/2013 | Horseman | G06F 19/3418 600/301 |
| 2013/0013327 | A1* | 1/2013 | Horseman | G06F 19/3418 705/1.1 |
| 2013/0117040 | A1* | 5/2013 | James et al. | 705/2 |
| 2014/0163333 | A1* | 6/2014 | Horseman | A61B 5/6887 600/301 |
| 2014/0275834 | A1* | 9/2014 | Bennett | B60N 2/919 600/301 |
| 2014/0353048 | A1* | 12/2014 | Kriger | B60N 2/002 177/1 |
| 2016/0163319 | A1* | 6/2016 | Parundekar | G10L 17/22 704/275 |

OTHER PUBLICATIONS

Guo et al. "Predicting overweight and obesity in adultgood from body mass index values in childhood and adolescence 1-3" 2002.*
Magarey et al. "Predicting obesity in early adulthood from childgood and parental obesity" 2003.*

* cited by examiner

GLOBAL OVERWEIGHT AND OBESITY PREVENTING AND TRACKING SYSTEM AND METHOD

CROSS REFERENCE TO RELATED APPLICATIONS

This application claims the benefit of U.S. Provisional Patent Application Ser. No. 60/939,810 filed May 23, 2007, the contents of which are incorporated herein by reference thereto.

FIELD OF THE INVENTION

The present invention relates to noninvasive obesity preventing methods and systems, particularly to those that analyze a weight trend of a person, forecasting overweight and obesity conditions that may begin in a short period of time (in several months or later) providing information of such weight trends to the person and/or to a health care professional.

BACKGROUND OF THE INVENTION

The problem of obesity is a nationwide problem. More than 65% of Americans (about 127 million adults) are overweight and 30% are considered obese (see www.obesity.org or www.cdc.gov). Approximately nine million American children ages 6-19 are considered overweight and 16% of American children are considered obese. The annual cost of overweight and obesity in the U.S. is more than $120 billion. As many studies show, we are living in a time of an obesity epidemic and the conclusion of such studies indicates that the main causes of obesity are bad nutrition and lack of physical activity. Therefore, in order to prevent obesity it is necessary for people to change their eating behaviors that will affect the change in body weight by including good nutrition and physical activity in their lifestyles.

It is clear that a proper nutritional plan and physical activity are the most important factors in dealing with obesity. It is also clear that recognizing obesity in its early stages is an important factor in dealing with obesity. If obesity is recognized in its early stage minor adjustments to the person's lifestyle may be sufficient to prevent the development of an obesity condition in an individual. Such a system may become a part of our mentality to reinforce our efforts to deal with obesity. Such an obesity preventing system will attempt to prevent obesity even when people are exposed to various human experiences (e.g., loss of a job, marriage, acquiring a new stressful job, etc.) that are life-changing. One of the signs of these changes occurring is a change in the health and usually the weight of a person.

There are two strategies that may be used to fight obesity. One is to treat people when they become obese. The second is to forecast obesity of a person by monitoring a weight trend of the person and creating a treatment plan to prevent obesity before the person becomes obese.

However, there is still a need for an obesity forecasting and preventing method and system.

SUMMARY OF THE INVENTION

In one exemplary embodiment, an obesity preventing and tracking system is provided, the system comprising: at least one in-building overweight and obesity preventing module for collecting anthropometry information from a person at a fixed location in order to forecast and prevent development of an obesity condition of the person; at least one on-board vehicle overweight and obesity preventing module for collecting the anthropometry information from the person in a vehicle operable by the person in order to forecast and prevent development of an obesity condition; at least one entertainment overweight and obesity preventing module for collecting anthropometry information from said person while said person is a guest at an entertainment facility in order to forecast and prevent development of an obesity condition; and a communications network for linking at least one in-building overweight and obesity preventing module and the at least one on-board vehicle overweight and obesity preventing module and the at least one entertainment overweight and obesity preventing module to a trend obesity preventing service for predicting the development of an obesity condition of the person.

In another exemplary embodiment, an obesity preventing and tracking system is provided, the system comprising: at least one in-building overweight and obesity preventing module for collecting anthropometry information from a person at a fixed location in order to forecast and prevent development of an obesity condition; at least one on-board vehicle overweight and obesity preventing module for collecting the anthropometry information from the person in a vehicle operable by the person in order to forecast and predict development of an obesity condition; and a communications network for linking at least one in-building overweight and obesity preventing module and at least one on-board vehicle overweight and obesity preventing module to a trend obesity preventing service for predicting and preventing the development of an obesity condition of the person.

In another exemplary embodiment, a method for determining if an individual is trending towards an obesity condition is provided, the method comprising: collecting information from an individual through at least one in-building overweight and obesity preventing module at a fixed location; collecting information from the individual through at least one on-board vehicle overweight and obesity preventing module from the person in a vehicle operable by the person in order to forecast and prevent development of an obesity condition; collecting information from at least one entertainment overweight and obesity preventing module from the person while the person is a guest at an entertainment facility; linking the at least one in-building overweight and obesity preventing module, the at least one on-board vehicle overweight and obesity preventing module and the at least one entertainment overweight and obesity preventing module; providing the collected information to a trend obesity preventing service; and predicting the development of an obesity condition of the person.

Accordingly exemplary embodiments of the present invention provide an obesity preventing and tracking system that forecasts a possibility of obesity of a person in a short period of time that allows a health care professional upon receiving prediction of a developing obesity condition from any module of the system to commence treatment of a person in any location much before any serious mental and body changes of the person take place. As a result, the health care provider has an opportunity to prevent obesity by slight lifestyle adjustments.

Overweight and obesity is not only a problem for adults. Recent data in children as young as 2 years old throughout adolescence have indicated a three-fold increase in overweight or obese conditions. The exemplary embodiments encourage a person, including children, to start any weight loss plan well before the overweight or obesity condition occurs. At the discretion of the user or parent, the prediction of the future possibility of overweight or obesity discovered in the system may be sent to the user's or child's primary doctor. The system may help to prevent obesity in any children's facility: school, college, kindergarten, university, home, etc.

By installing modules of the system in schools, daycares, etc., the health care provider can supervise a large number of children to predict and prevent overweight conditions because the system will collect and memorize children's weight measurements automatically without any effort from a doctor, and only a delegated non-medical person, such as a teacher or daycare worker, etc., will assist them in this procedure. The data collecting device of the system may also generate a personalized health card of the children and students.

The system may also help children and adults who are already overweight or obese by use of the system for monitoring their weight progress during a prescribed weight loss plan and correcting the strategy of the treatment by counting on the system's ability to forecast and to create behavior motivation for a good lifestyle and health. So by use of the system, a health care provider can drastically enhance the ability to communicate with children and adults, and one system may provide service for many children and adults in a college, university, school, kindergarten, medical facility, home, company, etc. by just one doctor or health care provider

BRIEF DESCRIPTION OF THE DRAWING

The above and other objects, features, and advantages will become more readily apparent from the following description, reference being made to the accompanying drawing in which.

DETAILED DESCRIPTION OF THE INVENTION

Figure 1:
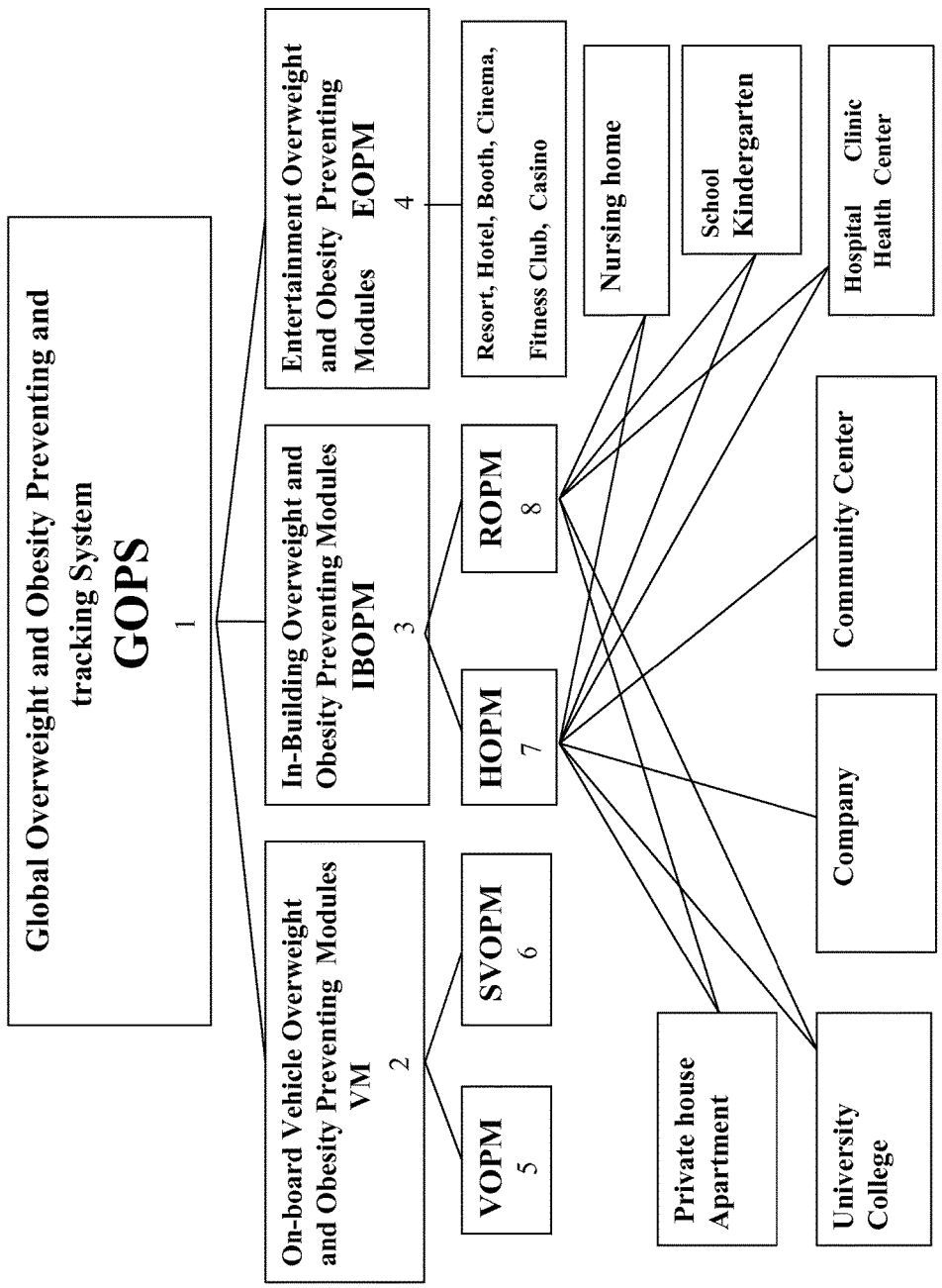
FIG. 1 is a block diagram of the Global Overweight and Obesity Preventing and tracking System (GOPS)

Reference is made to the following patents and/or patent applications: U.S. Pat. Nos. 6,649,848; 6,816,807; U.S. Patent Application No. 2005/0194192; and U.S. Provisional Patent Application No. 60/939,810 the contents each of which are incorporated herein by reference thereto.

In accordance with an exemplary embodiment of the present invention a method and system is provided that provides an accurate, user-friendly system to an individual and may forecast and prevent obesity of the individual. The system will forecast and prevent obesity of the individual by acquiring and analyzing aggregate information about the weight and height trends of any age individual spending time enough in any place.

Another exemplary embodiment of the present invention allows to employ anthropometry measurements of a person acquired by any part of a Global Tracking Overweight or Obesity Preventing System (GOPS) where a person may stay temporary during a business trip, vacation, etc. (e.g., Entertainment Overweight and Obesity Preventing Module (EOPM) in a resort or hotel), at home, medical facility, work, etc. (e.g., Hidden Overweight and Obesity Preventing Module (HOPM) or Resting Overweight and Obesity Preventing Module (ROPM)) or when a person is driving (e.g., Vehicle Overweight and Obesity Prevention Module (VOPM) or Vehicle Self-Acquiring Overweight and Obesity Preventing Module (SVOPM)) or any other module of a GOPS. Another exemplary embodiment allows a health care professional upon receiving prediction of a developing obesity condition of a person from any part of the GOPS system to commence treatment of this person much before any serious mental and body changes of the person take place.

Right now only the following options are available to deal with obesity:

1) Treat people that are already obese, this method is expensive and not efficient;

2) Predict overweight and obesity of people who are not overweight or obese yet but may have propensity for this problem and start adjustment of their lifestyle.

A Comprehensive Obesity Prevention Technology (C-OPT) that expands the second option to all people by predicting trend to overweight or obesity in a short period of time and start treatment much before a person will become overweight or obese is provided by the present invention. C-OPT technology helps to monitor, identify, and prevent problematic trends towards obesity in people's Body Mass Index (BMI), and alerts one's health care provider when there is a possibility that such a condition may develop in a short period of time.

According to "The Guide to Clinical Preventive Services 2007. Recommendations of the U.S. Preventive Services Task Force", "Body mass index (BMI), which is simply weight adjusted for height, is a more practical and widely-used method to screen for obesity. Increased BMI is associated with an increase in adverse health effects. Expert committees have issued guidelines defining overweight and obesity based on BMI. Persons with a BMI between 25 and 29.9 are overweight and those with a BMI of 30 and above are obese. BMI is calculated either as weight in pounds divided by height in inches squared multiplied by 703, or as weight in kilograms divided by height in meters squared." (The Guide to Clinical Preventive Services 2007. Recommendations of the U.S. Preventive Services Task Force. U.S. Department of Health & Human Services. Agency for Healthcare Research and Quality.)

As a result, the health care provider has an opportunity to prevent obesity way before the person becomes obese by slight lifestyle adjustments. In exemplary embodiment of the present invention C-OPT technology was used in design of several modifications of Obesity Prevention Modules such as an on-board Vehicle Self-acquiring Overweight and Obesity Preventing Module (SVOPM); and in-building Hidden Overweight Prevention Module (HOPM) that is convenient to use home, at work, at educational or medical facilities, etc.

In yet another exemplary embodiment of the present invention a noninvasive overweight and obesity preventing method is used for overweight and obesity preventing goal in an Entertainment Overweight Preventing Modules (EOPM) in a resort, hotel, fitness club, in a shop, in a cinema, etc. which is a part of the GOPS.

Another exemplary embodiment of the present invention that each weight news sender calculates a time period (number of days DH) between height measurements of a person depending on his/her age.

Exemplary embodiments of the present invention provide a method for forecasting overweight and obesity of an individual who is not yet overweight but may have a propensity for developing such a condition by employing a Comprehensive Obesity Prevention Technology (C-OPT). The C-OPT efficiently screens for overweight or obesity conditions by analyzing trends, and based on those trends, implementing a treatment plan to prevent an individual from becoming overweight or obese. One main objective of C-OPT technology is to help monitor, identify and prevent problematic trends in an individual's Body Mass Index (BMI) that relate to developing an overweight or obesity condition, and quickly alerting the individual's health care provider when there is a possibility that such a condition may develop. BMI, which is simply weight adjusted for height, is a more practical and widely used method to screen for obesity. Increased BMI is associated with an increase in adverse health effects. Expert committees have issued guidelines defining overweight and obesity based on BMI. Persons with BMI between 25 and 29.9 are overweight and those with a BMI of 30 and above are obese. BMI is calculated either as weight in pounds divided by height in inches squared multiplied by 703, or as weight in kilograms divided by height in meters squared.

The BMI percentile for age and sex is the preferred method to screen for overweight and obesity conditions in children and adolescents because of its feasibility, reliability, and tracking with adult overweight and obesity measures. BMI values in the growth charts for children and adolescents are Centers for Disease Control and Prevention (CDC) population-based references for comparison of grown distribution to those of a larger population. The growth charts consist of a series of percentile curves that illustrate the distribution of selected body measurements in U.S. children. Pediatric growth charts have been used by pediatricians, nurses and parents to track the growth of infants, children and adolescents in the United States. Data used to produce the United States Growth Charts' smoothed percentile curves are contained in data files representing the growth curves BMI for age and sex. (e.g., see cdc.gov/nchs/about/major/nhanes/grothcharts/datafiles.htm).

Exemplary Embodiments of the present invention provide that being at risk for being overweight is defined as a BMI between the 85th and 94th percentile for age and sex, and being overweight is defined as a BMI over the 95th percentile for age and sex. Hereinafter, exemplary embodiments of the present invention incorporate these BMI cuts off points for overweight and obesity conditions into each module of the GOPS. Of course, other ranges are considered to be within the scope of exemplary embodiments of the present invention.

Exemplary embodiments of the present invention implement C-OPT technology into any module of a Global Tracking Overweight or Obesity Preventing System (GOPS) such as an on-board Vehicle Self-acquiring Overweight and Obesity Preventing Module (SVOPM), and/or in-building Hidden Overweight Prevention Module (HOPM) that is convenient for use at home, work, educational or medical facilities, etc., and/or Entertainment Overweight Preventing Modules (EOPM) convenient for use in a resort, hotel, fitness club, in a shop, in a cinema.

Exemplary embodiments of the present invention allows a GOPS and method that can be equipped by Inside-Building Overweight and Obesity Preventing Modules (IBOPM), and/or on-board Vehicle Self-acquiring Overweight and Obesity Preventing Modules (SVOPM), and/or Entertainment Overweight and Obesity Preventing Modules (EOPM) to provide convenient collecting of anthropometry information acquired by weighing apparatuses located in a vehicle, at home, in a street, in medical facility, etc. from users of any above mentioned module for predicting of a developing overweight or obesity condition of a person and automatically warning a person and a healthcare professional of a developing an obesity condition and sending said information for processing and predicting of a developing obesity condition.

Another exemplary embodiment of the present invention is that the GOPS system provides two types of services that memorize and process the anthropometry measurements:

Local Trend Obesity Preventing Service (LoTOPS) that is located in the weight and height news senders of each Module and main Trend Obesity Preventing Service (TOPS) that includes the main database of the GOPS system. All anthropometry and personal data of each user of GOPS are memorized in main database of the GOPS system independently of how many modules of SVOPS, HOPS, ROPS, or EOPS are used.

Another exemplary embodiment of the present invention is that the anthropometry and personal data of each child in kindergarten or school and college student will be submitted to the GOPS system at the person's discretion or at the discretion of an anthropometry assistant in an education facility depending on the age of the student.

Another exemplary embodiment of the present invention is that for a correct weighing of a person by a SVOPS Module a switch is inserted in a back of the car seat. This switch will signal to the SVOPS Module if a person's back will touch the back of the car seat during a person's weight measurement.

Another exemplary embodiment of the present invention allows a person to prove that he/she is a real legal owner and user of a module of GOPS by inputting his/her identity data unit into a weight and height news sender by employing his/her user name and password; and/or bar code sensor; and/or fingerprint reader. Here GOPS memorizes and stores all anthropometry measurements and personal data of each user of the GOPS system in at least two types of services: (1) Local Trend Obesity Preventing Service (LoTOPS) that is located in the Height and Weight News Sender (HEWENS) of each module and (2) main Trend Obesity Preventing Service (TOPS) that includes the main database of the GOPS system. All anthropometry measurements and personal data of each GOPS user are memorized and stored in the GOPS database, independently of how many modules of the GOPS system are used (e.g., SVOPS, HOPS, ROPS or EOPS).

One main objective of the EOPM of the exemplary embodiments of the present invention is to help people prevent obesity conditions when they can't use an SVOPM and an IBOPM. For this purpose, an EOPM may include a vending machine (weighing vending automat) with a flow chart of an overweight and obesity preventing method that is accommodated for entertainment purposes. The user of the EOPM may only wish to measure his/her weight and to use the result of weighing in his/her home Hidden Overweight and Obesity Preventing Module (HOPM) in several days when the user returns home after a business trip or vacation because the user does not want to view any health care information currently while being in a resort or in a hotel, a hidden obesity preventing method may be used. If the user of the EOPM wishes to measure his/her weight and/or height and to see any health care information, a two way entertainment obesity preventing method communication may be used.

Another exemplary embodiment of the present invention that weighing device of weight sender employs an exchanged order of weighing and calibration steps that makes weighing process of a person more accurate and faster.

The entertainment part EOPM of the GOPS not only weighs an individual, predicts his/her overweight or obesity condition, etc., but serves as a source of an entertainment that may improve the mood or disposition of an individual being in different places, encourage him/her in their challenge to improve and keep their health in good condition, and provide information that may improve a mood of an individual. The SVOPM of the GOPS not only weighs an individual, predicts his/her overweight or obesity condition, etc., but serves as a source of an entertainment that may improve a mood of an individual in a vehicle, encourage him/her in their challenge to improve and keep health in good condition. For example, during heavy traffic the Self-acquiring on-board Vehicle Overweight and Obesity Preventing Module may provide information that may improve the mood or disposition of a driver by showing a graph of weight. In addition, if a person made progress in a weight loss program, the system may encourage the person by singing a song, reading an article, telling a joke, etc. The other advantageous feature of the EOPM is that while people pay attention to measuring their weight, they can control their weight more often and may be helpful in preventing a potential obesity condition.

Referring now to FIG. 1 a block diagram of a Global Overweight and Obesity Preventing and Tracking System (GOPS) 1 is illustrated. In one non-exemplary embodiment, the system 1 may consist of three parts. These parts may be: (1) an On-board Vehicle Overweight and Obesity Preventing Modules (VM) 2, (2) an In-Building Overweight and Obesity Preventing Modules (IBOPM) 3 and (3) an Entertainment Overweight and Obesity Preventing Modules (EOPM) 4 each of which are in data communication with the main Trend Obesity Preventing Services (TOPS) 30 of GOPS via a local or Internet network or any other suitable means of data transmission. As used herein data transmission or communication refers to operable communication of data either one way or two way between the various system elements of exemplary embodiments of the present invention and is depicted by lead lines or arrowhead lines, which illustrate a means for either signal communication or mechanical operation, depending on the system element involved. Operable communication amongst and between the various system elements may be obtained through a hardwired or a wireless arrangement. Each system and/or component or module (e.g., GOPS, EOPM, HOPM, ROPM, VOPM, SVOPM, IBOPM, TOPS, LoTOPS, HEWENS, BEHEWENS, WENSEPN, WTA, etc.) may comprise a standalone computer or a network computer, microcontroller or integrated microprocessor and may include instructions in a variety of computer languages for use on a variety of computer platforms, such as, for example, PC, Apple or Sun Microsystems, and under a variety of operating systems, e.g. Windows, MacOS, and Unix or the like. Other examples of the computer include a system having a microprocessor, microcontroller or other equivalent processing device capable of executing commands of computer readable data or program for executing a control algorithm. In order to perform the prescribed functions and desired processing, as well as the computations therefore (e.g., the execution of fourier analysis algorithm(s), algorithm steps identified in the flowcharts, the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

The VM 2, the IBOPM 3, and the EOPM 4 employ a method of having an individual being weighed and having certain additional features.

The VM 2 may consist of a VOPM 5 and a SVOPM 6. The IBOPM 3 consists of a Hidden Overweight and Obesity Preventing Modules (HOPM) 7 and a Resting Overweight and Obesity Preventing Modules (ROPM) 8. The HOPM 7 and the ROPM 8 are in direct communication with several different entities that may include among other things a private house or apartment, a university or college, a company, a community center, a nursing home, a school, kindergarten, and/or a hospital or clinic.

The EOPM 4 is in direct communication with, for example, a resort, casino, hotel, booth in a street or a fitness club or a cinema shop.

Figure 2:
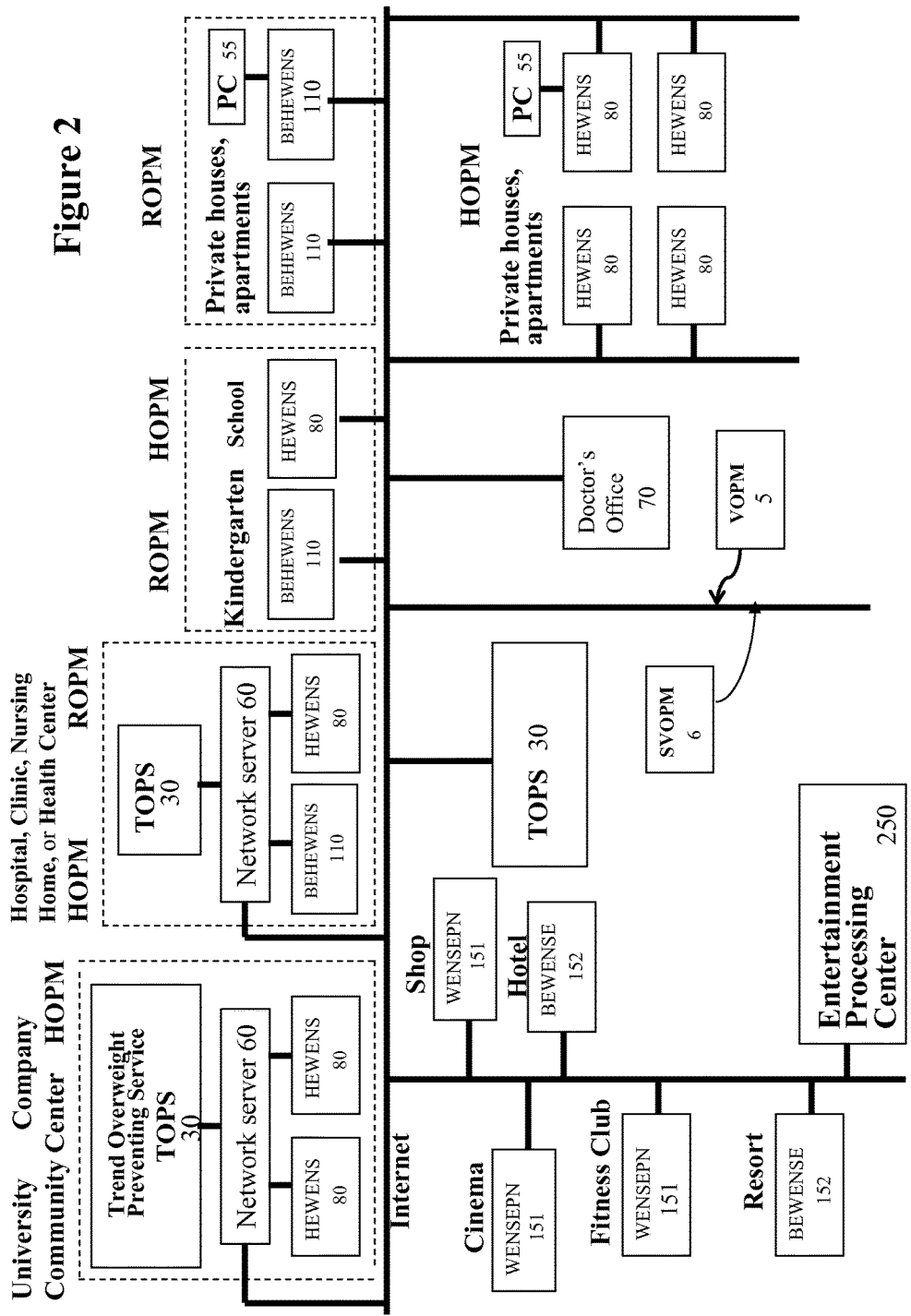
FIG. 2 is a structure of the Global Overweight and Obesity Preventing and tracking System in an exemplary embodiment.

FIG. 2 illustrates different types of a vehicle module VM (e.g., VOPM 5 and SVOPM 6 of FIG. 1) in the Global Overweight and Obesity Preventing and Tracking System (GOPS) structure. The VOPM 5 utilizes a weighing device connected to a seat of the driver or passenger. The SVOPM 6 utilizes a first weighing device connected to a seat of the driver or passenger and a second weighing device upon which the feet of the driver or passenger may be placed.

After the required measurements of weight have completed and recorded, they are sent to the small Local Trend Obesity Preventing Service (LoTOPS) 75 of the VOPM 5 or SVOPM 6 through an internal bus that will serve to vehicle owner or family only. LoTOPS 75 consists of a client database (CD) 76 and a Weight Trend Analyzer (WTA) 77. The client database automatically collects the name, age, sex, weight, height, and other information of the person. The (CD) 76 automatically collects the name, age, sex and weight, height, etc. of the person in the seat of the VOPM 5 or SVOPM 6. The WTA 77 has in its memory a recommended BMI for the person depending on age, sex, and height of the person. WTA 77 receives the current weight of the person from the CD 76 and creates a graph of the person's BMI progress and compares it to a recommended BMI progress graph. The WTA 77 then determines if the person's BMI trends move towards an overweight or obesity condition. If the WTA 77 discovers after acquiring a certain number of anthropometry measurements that the person or his/her children are becoming overweight or obese, the module sends a warning message (e.g., Special Overweight or Obesity Signal—S.O.S.) to a person at the discretion of that person or parent of child who is developing an overweight or obesity condition analyzed by the LoTOPS service, wherein an authorization input is required to authorized transmission of the data.

Simultaneously the anthropometry measurements are sent outside to the Trend Obesity Preventing Service (TOPS) 30 of GOPS through a wireless data transmission communication device 15, Internet connection or any other suitable means of data transmission. Once this information is received and analyzed by the TOPS service 30, at the discretion of that person or parent of child whose measurement were recorded an appropriate warning is issued to an individual's healthcare professional if an overweight or obesity condition is predicted.

Figure 3:
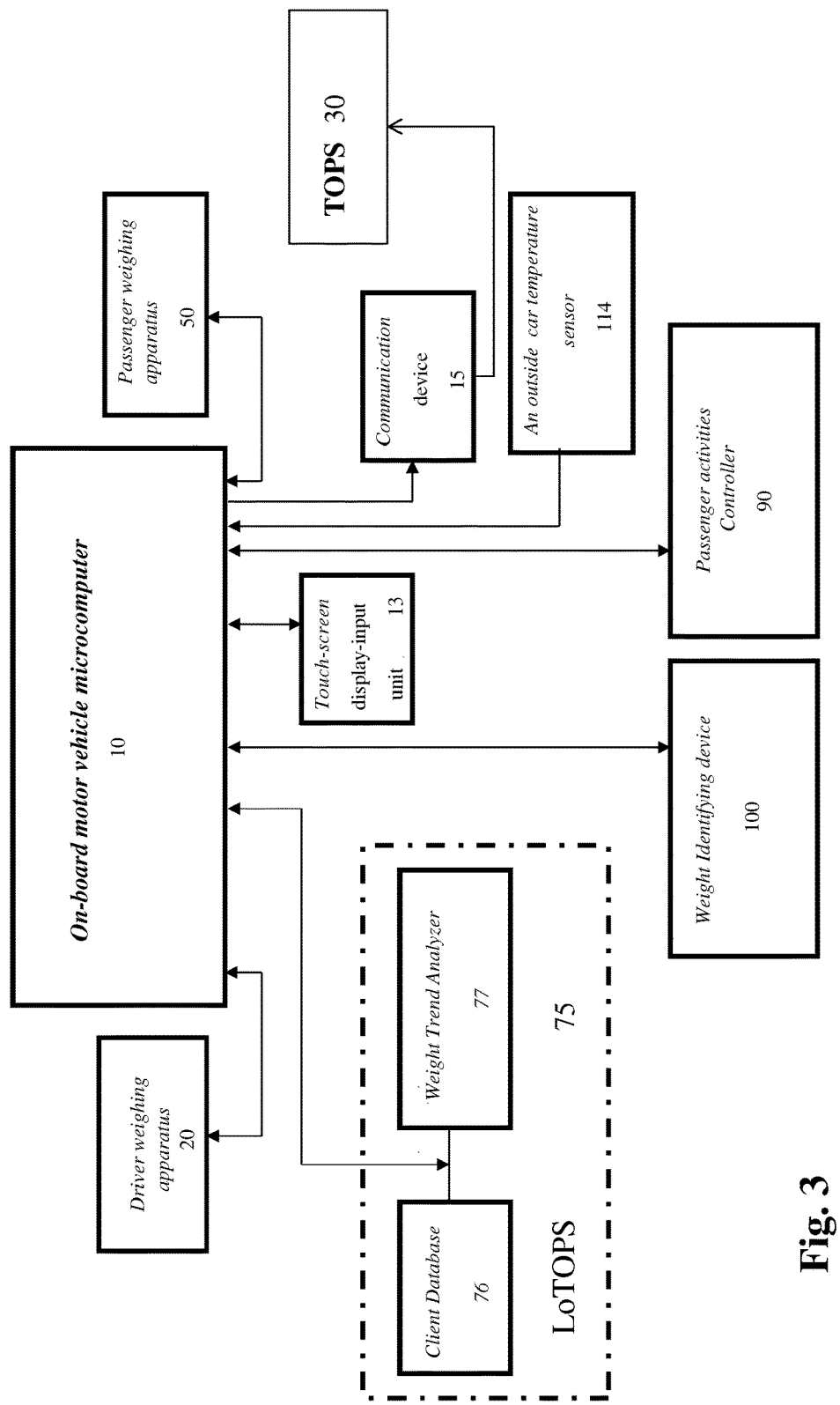
FIG. 3 is a simplified block diagram of an on-board Vehicle Self-acquiring Overweight and Obesity Preventing Module (SVOPM)

TOPS 30 consists of a client database (CD) 11 and a WTA 16. The client database automatically collects the name, age, sex, weight, height, etc. and other information of the user of VOPM 5 or SVOPM 6 through any data transmission medium (e.g., wireless or wired and equivalents thereof). The WTA 16 has in its memory a recommended BMI for the person depending on age, sex, and height of the person. The WTA 16 receives the current weight of the person from the CD 11 and creates a graph of the person's BMI progress and compares it to a recommended BMI progress graph. After acquiring a certain number of anthropology measurements the WTA 16 then determines if the person's BMI trend moves towards an overweight or obesity condition. If the WTA 16 determines that after acquiring a sample of anthropometry measurement, that the person is trending towards an overweight or obese condition, the GOPS sends a warning message (e.g., Special Overweight or Obesity Signal—SOS) to the person's health care provider or office 70 at the discretion of that person or a parent of that person if the person is a child. The health care professional may contact the person and explain the reason(s) for calling and accordingly request that the driver or passenger to schedule an appointment for a physical. After the health care professional conducts a physical and he/she discovers the reason of the potential obesity condition and the health care professional may suggest to the person slight adjustments to his/her lifestyle or give a referral to the dietitian or nutrition specialists. Thus, healthcare professionals have an opportunity to start treatment of a potentially obese person before any serious mental and body changes may occur. FIG. 3 illustrates a block diagram of a SVOPM. The SVOPM comprises an on-board vehicle microcomputer 10 programmed to provide a method of forecasting obesity, a touch screen display-input unit 13, a wireless communication device 15, an on-board driver weighing apparatus 20, a passenger weighing apparatus 50, a passenger activities controller 90, and a weight identifying device 100. The SVOPM commences its operation as the vehicle's operator pushes a button in the vehicle's keyless remote control located outside of the vehicle. Microcomputer 10 controls "zero" adjustment of both the driver weighing apparatus 20 and the passenger weighing apparatus 50. The passenger activities controller 90 is designed to serve a passenger. The weight identifying device 100 helps to determine the reason of a person's weight change from a previous measurement exceeding a certain magnitude, ascertains whether there has been a change in clothing or footwear since the previous measurement processing a correlation of the separate measurements of the body and foot parts of the person's weight and by a dialogue with the person and checking the temperature sensor 114 and memorizing it's output for creating data that correlates clothing or footwear to outside car temperature. The weight identifying device 100 provides resources for supporting a dialogue between a driver or passenger and the SVOPM. The driver or passenger can answer or respond to the SVOPM by touching the touch screen display-input unit during these dialogues. When the driver sits in the driver car seat, the driver weighing apparatus 20 measures his/her weight. When a passenger sits in the passenger car seat, the passenger weighing apparatus 50 measures his/her weight. If the module is activated, the personal driver or passenger data is memorized. If the driver or passenger is not a new user, the module recognizes if the weight of the person has changed by five or more pounds since the last measurement were taken. Of course, one skilled in the art can determine that other weight ranges can be programmed into the unit. The module figures out the reason for this change of the person's weight by the dialog between system and person. If the weight has changed because of the clothing or footwear change, the module memorizes the weight of new clothing and footwear. When SVOPM collects weight measurements of a person or his/her children (i) it may assess a future trend of weight progress, and (ii) it may define a probability of an obesity condition of a person or his/her children. If any such obesity conditions are deemed to exist, the SVOPM does not send any warnings to a person immediately. In contrast, the SVOPM may send a warning to the person at the person's discretion at assigned time.

A basic structure of a Weighing Apparatus (WAPP) of a SVOPM may use two weighing devices for weighing an individual in a vehicle. A weighing platform of the first weighing device may be located in an individual's car seat and can measure the weight of a portion of the individual's body located in the car seat. The weighing platform of a second weighing device of the WAPP can measure the weight of the feet portion of the individual's body, and can be fixed or retractable from any suitable part of a vehicle or located in a car mat under the feet of an individual. To weigh a driver, the WAPP checks if a driver is in the car seat by processing any changes in the data received from the weighing device in a driver car seat and can thus continue to monitor the weight of the driver until the driver sits in the car seat. After that the WAPP checks if a gear selector is in the "Park" position. If the gear selector is in a parking position, the WAPP checks to determine if the driver's feet are on a weighing platform of the second weighing device by processing any changes in the data received from the second weighing platform. If the driver's feet are on a platform of the second weighing device, the WAPP starts the weighing operation and memorizes the driver's weight. The result of weighing is equal to a sum of a portion of the weight of a driver applied to the driver car seat and a portion of the weight of a driver applied to the weighing platform of the second weighing device. The structure of the WAPP for weighing a passenger is the same as for weighing a driver.

Figure 4:
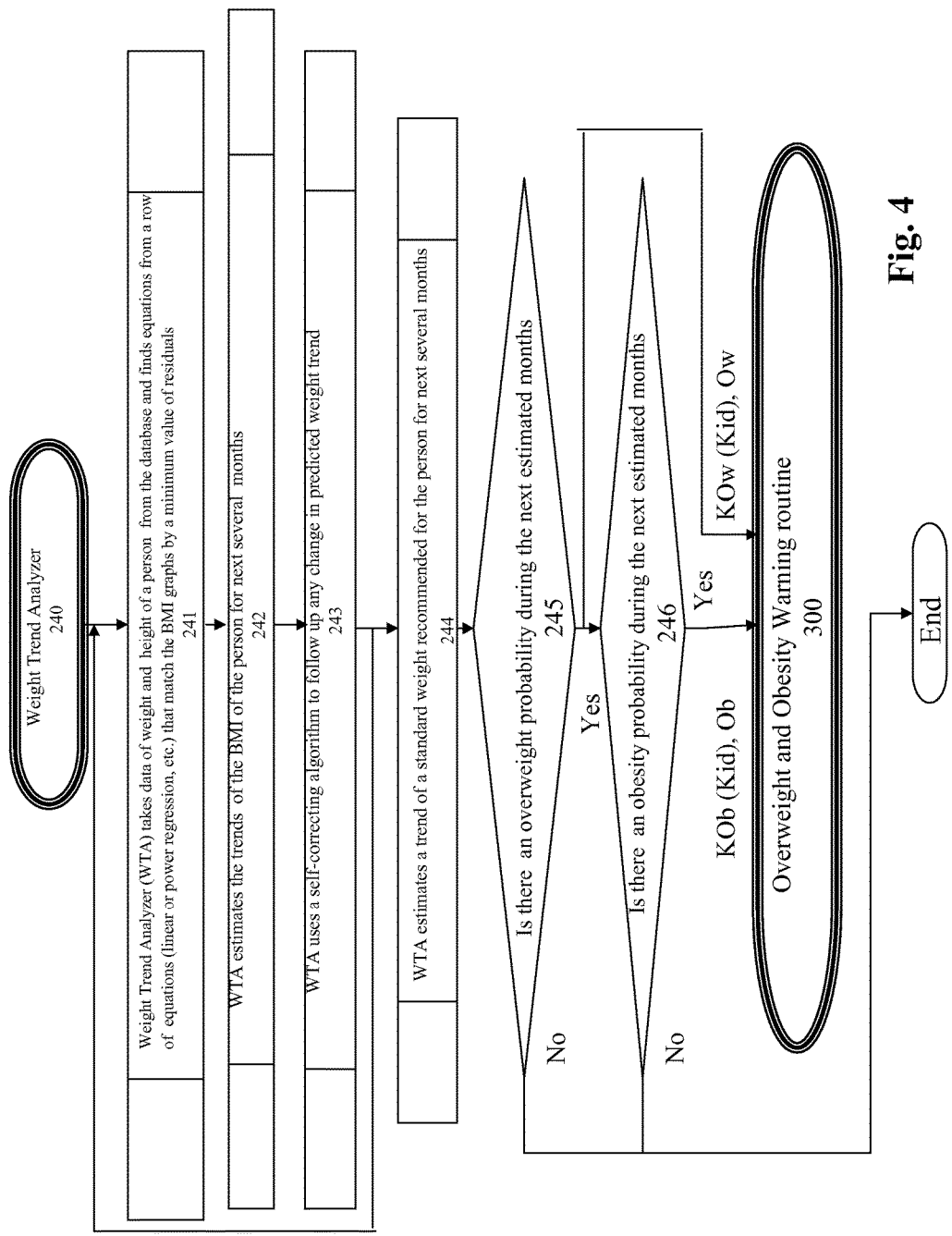
FIG. 4 is a flowchart for the Weight Trend Analyzer routine or algorithm resident upon a microprocessor or memory of a module of an exemplary embodiment of the present invention.

FIG. 4 shows a flowchart 240 for the Weight Trend Analyzer (WTA) routine or algorithm resident upon a microprocessor or memory of a module of an exemplary embodiment of the present invention, the routine comprising a series of executable steps of machine code. The flowchart 240 collects measurements of weight and height of a person and estimates an overweight or obesity probability of a person during the next several months by using a Body Mass Index (BMI) of a person.

Body Mass Index (BMI) percentile for age and sex is the preferred measure for detecting overweight in children and adolescents because of its feasibility, reliability, and tracking with adult obesity measures. BMI values in the growth charts for children and adolescents are Centers for Decease Control and Prevention (CDC) population-based references for comparison of growth distribution to those of a larger population. The growth charts consist of a series of percentile curves that illustrate the distribution of selected body measurements in U.S. children. Pediatric growth charts have been used by pediatricians, nurses, and parents to track the growth of infants, children, and adolescents in the United States. Data used to produce the United States Growth Charts smoothed percentile curves are contained in data files representing the growth curves BMI-for-age and sex.

International cut off points for BMI for overweight and obesity by sex for children and adolescents between 2 and 18 years, defined to pass through body mass index of 25 and 30 kg/m2 at age 18, obtained by averaging data from Brazil, Great Britain, Hong Kong, Netherlands, Singapore, and United States and provided in "Establishing a standard definition for child overweight and obesity worldwide: international survey" by Tim J Cole, Mary C Bellizzi, Katherine M Flegal, William H Dietz, *BMJ* 2000; 320:1240 (6 May). Herein-after in the present patent application BMI cut off points of adult and children overweight and obesity are referred for each module of the GOPS. In step 241, the WTA, by collecting measurements of weight and height of a person, finds equations that match the BMI graphs, the equations being stored in memory of the WTA. After that, the WTA estimates, in step 242, the trends of the BMI of the person. To improve the correctness of the calculated BMI trend, the WTA employs, in step 243, the results of the previous calculation of the trend. In step 244, the WTA estimates a trend of BMI recommended for a person and a probability of a person's obesity during the following months. If a possibility of an overweight condition is detected, as in step 245, or if a possibility of an obesity condition is detected, as in step 246, the WTA sends appropriate warning signals (e.g., Kob—obesity of a kid, Ob—obesity of a person, KOw—overweight of a kid, Ow—overweight of a person, etc.) to an Overweight and Obesity Warning routine 300 or algorithm resident upon a microprocessor or memory of a module of an exemplary embodiment of the present invention.

Figure 5:
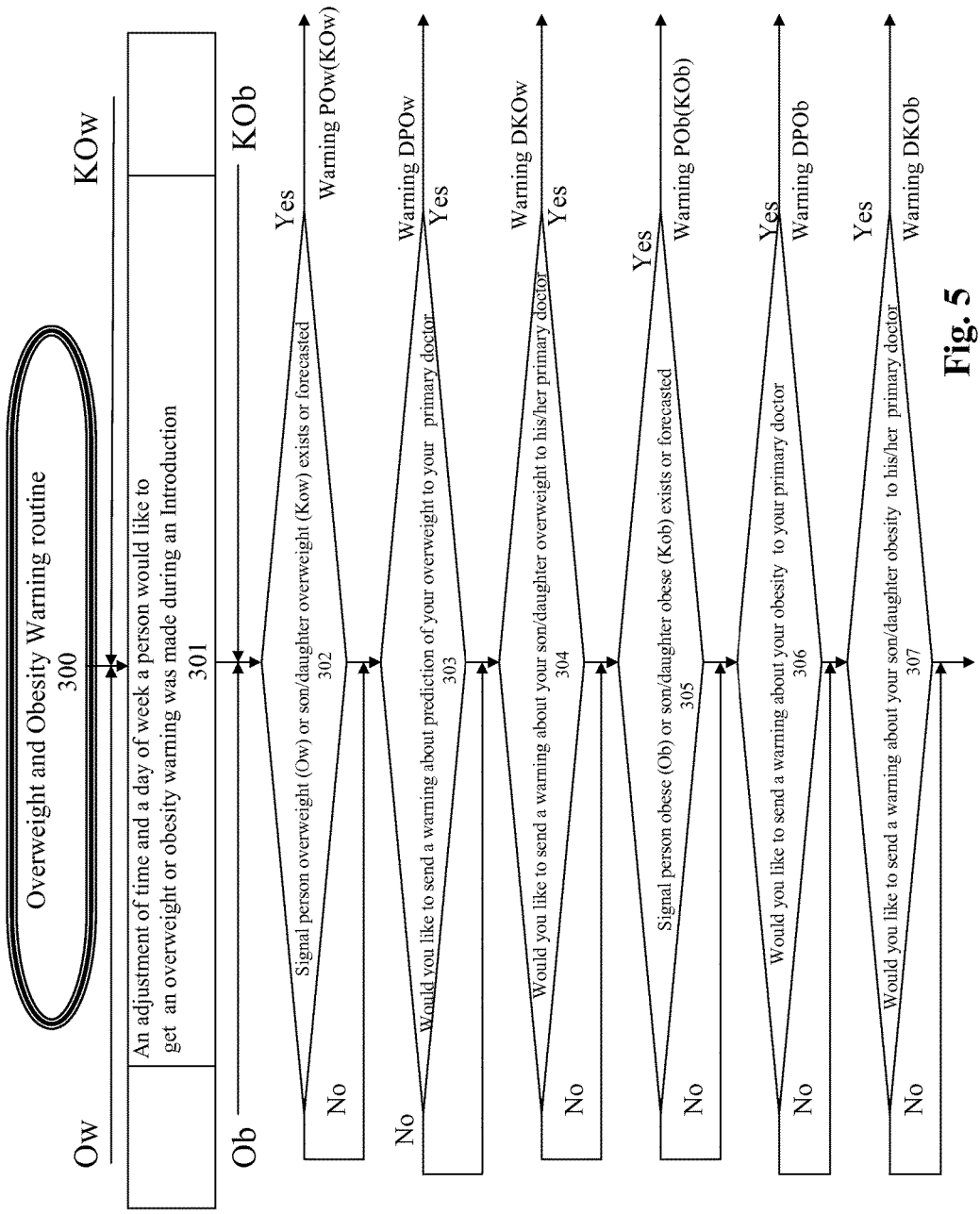
FIG. 5 is a flowchart for the Overweight and Obesity Warning routine or algorithm resident upon a microprocessor or memory of a module of an exemplary embodiment of the present invention.

FIG. 5 illustrates a flowchart for the Overweight and Obesity Warning routine. At step 301, an adjustment of time and a day of the week that a person would like to obtain an obesity warning is made. This routine, at the person's discretion, sends overweight or obesity warnings from steps 302 to 307 to a person (e.g., POw, POb) whose overweight or obesity condition exists or forecasted and/or to a primary doctor of a person (e.g., DPOw, DPOb), to owner of a car whose child's or teenager's overweight or obesity condition exists or forecasted (e.g., KOw, KOb), or to a primary doctor of a person's child (e.g., DKOw, DKOb).

Figure 6:
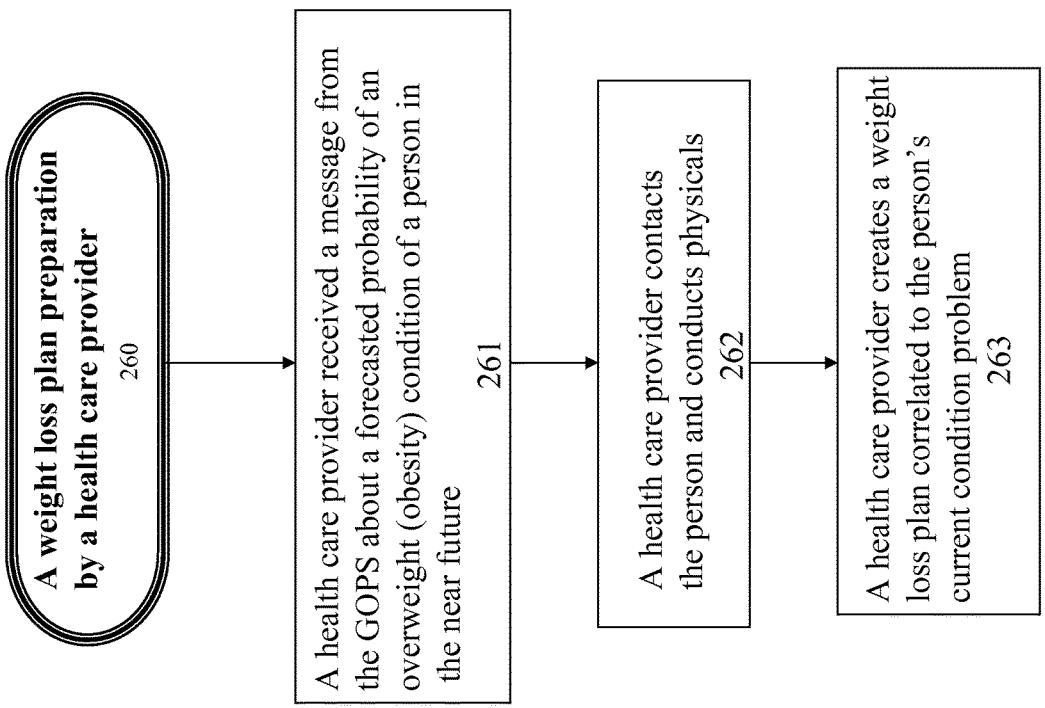
FIG. 6 is a flowchart for creation of a weight loss plan.
Figure 7:
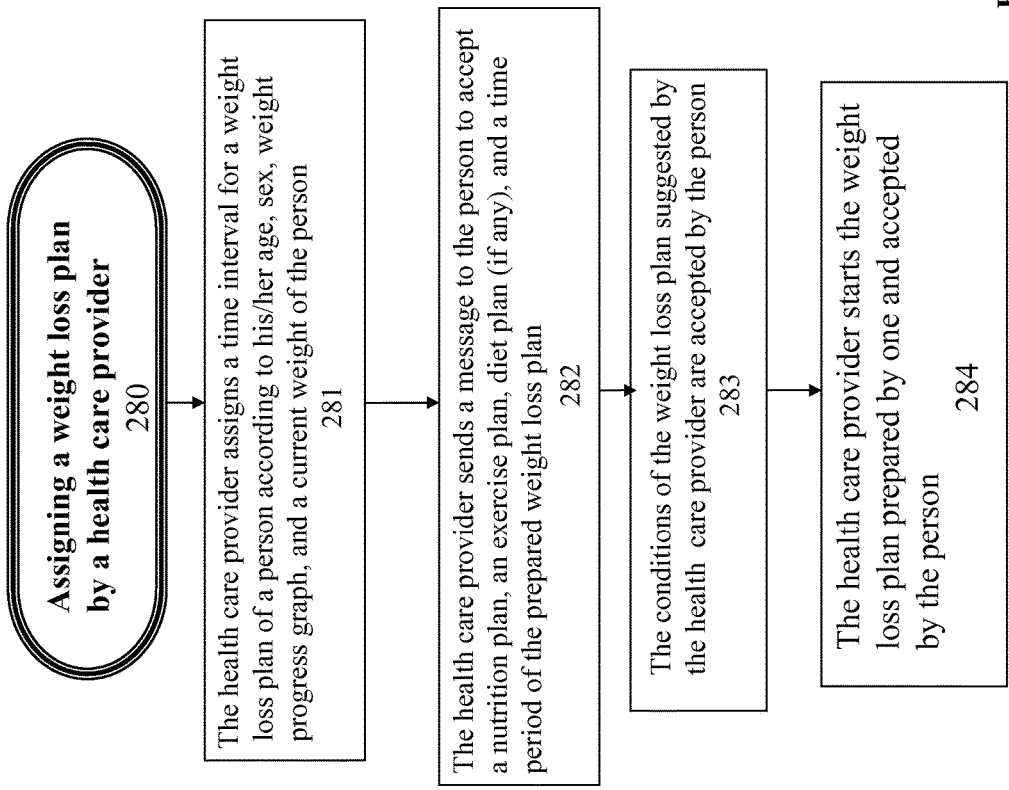
FIG. 7 is a flowchart assignment of a weight loss plan by a health care provider.

FIG. 6 and FIG. 7 provide a convenient explanation of a possible communication of an involved health care provider with the GOPS.

FIG. 6 shows a flowchart 260 of health care provider's possible steps taken in preparation of a person's weight loss plan after receiving a message from the GOPS about a forecasted probability of an overweight or obesity condition of a person in the near future. FIG. 7 shows a flowchart 280 of health care provider possible activities for assigning a nutrition plan, an exercise plan, diet plan (if any), and a time period of the weight loss plan after receiving a message from the GOPS about a forecasted probability of an overweight or obesity condition of a person. In 262 a health care provider contacts a person and conducts physicals. As result of these activities, the health care provider finds out the source of a negative weight trend of the person. Subsequently the healthcare provider makes a decision as to how to start to treat the person for preventing an overweight or obesity condition. The health care provider creates a weight loss plan correlated to correct the factors of the person current condition problem in step 263.

In step 281 of FIG. 7, the health care provider assigns a time interval for a weight loss plan of a person according to his/her age, sex (only for children and adolescents), weight progress graph, and current weight. In step 282 the health care provider sends a message to the person to accept a suggested a nutrition plan, an exercise plan, diet plan (if any), and a time period of the prepared weight loss plan. The person has the option of accepting or rejecting the conditions of the suggested weight loss plan, and if the conditions of the weight loss plan suggested by the health care provider are accepted in 283 by the person, the health care provider starts in 284 the prepared weight loss plan. When a time interval of a weight loss plan ends, the health care provider may analyze the condition of the person once more. Because the WTA in step 240 continues to monitor a weight trend of the person during the weight loss plan 280 started by the health care provider, and if the result of the weight loss plan is negative, the WTA accordingly sends warning signals (e.g., Kob—obesity of a kid, Ob—obesity of a person, KOw—overweight of a kid, Ow—overweight of a person) to the Overweight Warning routine 300 (shown in FIG. 5). This routine at person's discretion sends warnings from steps 302 to 307 of FIG. 5 to a person (e.g., POw, POb), to a primary doctor of a person (e.g., DPOw, DPOb), to owner of a car whose child or teenager is overweight or obese or these conditions are forecasted (e.g, KOw, KOb), or to a primary doctor of a person's child (e.g., DKOw, DKOb) who is overweight or obese or the possibility of becoming overweight or obese is forecasted.

When the SVOPM is activated, the screen "Welcome to SVOPM" appears in FIG. 8 described below.

Figure 8:
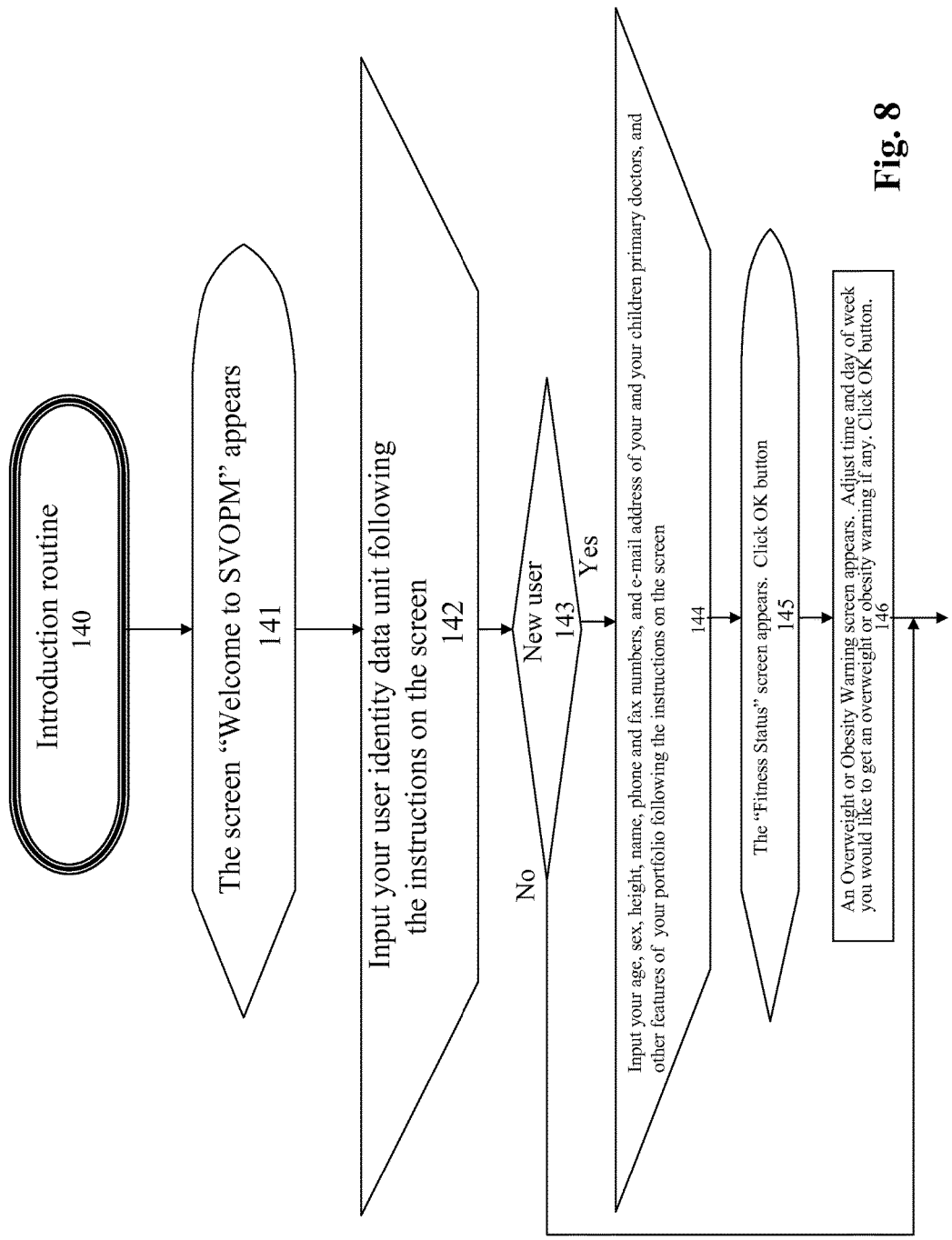
FIG. 8 is a flowchart for the Introduction routine or algorithm resident upon a microprocessor or memory of a module of an exemplary embodiment of the present invention.

FIG. 8 shows a flowchart for the Introduction routine 140 or algorithm resident upon a microprocessor or memory of a module of an exemplary embodiment of the present invention. The Introduction routine 140 commences with the screen "Welcome to SVOPM" at step 141. At step 142, the person is invited to input his/her identity into the data unit. The module checks the identity data unit and recognizes if the person is a new user at step 143. If the person is a new user, the module requests the person to input, at step 144, his or her age, sex, height, name and e-mail address or phone and fax numbers and other contact information of his/her and his/her children's health care providers and other things of his/her portfolio following the instructions on the screen. After the person has entered the above data, the "Fitness Status" screen appears at step 145. The "Fitness Status" screen shows the recommended weight for this person. An Overweight and Obesity Warning screen appears at step 146. A person is invited to enter the time and day of the week that the person would like to receive an overweight or obesity warning, if any. This means that any overweight or obesity warning (e.g., to the person, to his/her primary doctor, or to his/her children's primary doctor, etc.) may be sent only at person's discretion. With regards to FIG. 3, the communication device 15 of the SVOPM includes peripherals and wireless network service devices for communication with other modules of GOPS.

Figure 9:
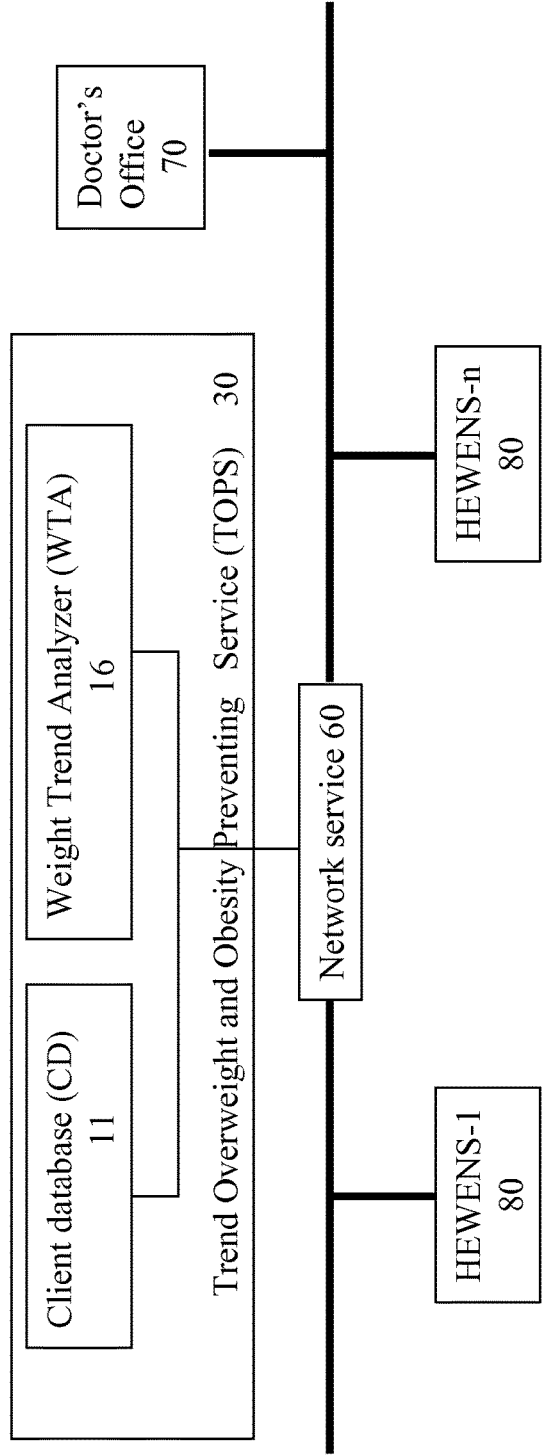
FIG. 9 is a block diagram of the Hidden Overweight and Obesity Preventing Module (HOPM) structure.

FIG. 9 shows a block diagram of the Hidden Overweight and Obesity Preventing Module (HOPM) according to an exemplary embodiment of the present invention. The HOPM module comprises a plurality of apparatuses for collection of data and a one-way automatic data transmission (e.g., via data transfer means, e.g., local network, Internet, or wireless communications, etc.) to a main data service. The apparatuses are capable of being packaged in a convenient power-controlled weight and height measuring device and adapted to interface with a main service. The module shown in FIG. 9 communicates with a trend overweight and obesity preventing service (TOPS) 30, which may be a personal computer (PC), and which may interact with other modules of the GOPS. TOPS 30 will be included in a structure of HOPM if HOPM is employed as a stand alone overweight and obesity preventing system HOPS. The main objective of this service is to collect the weight and height data automatically from patients through a plurality of Height and Weight News Senders devices 80 (HEWENS) by using a data transfer means such as a network service 60 configured to receive and disperse the collected information. The HEWENS device is an automatic device that is activated by an individual when he/she steps on a weight and height measuring platform. After the required measurements of weight and height (periodically) have been completed, they are sent to the small Local Trend Obesity Preventing Service (LoTOPS) 75 of the HEWENS device 80 through an internal bus. The Local Trend Obesity Preventing Service (LoTOPS) 75 serves to HEWENS device 80 users only and depends on the preferences of the users of the HEWENS to monitor their weight trend at home, in medical facility, school, etc. or not to monitor.

LoTOPS 75 consists of a client database (CD) 76 and a Weight Trend Analyzer (WTA) 77. The client database automatically collects the name, age, sex, weight, height, and other information of the person. The WTA 77 has in its memory a recommended BMI for the person depending on age, sex, and height of the person. WTA 77 receives the current weight and height (anthropometry measurements) of the person from the CD 76 and creates a graph of the person's BMI progress and compares it to a recommended BMI progress graph. The WTA 77 then determines if the person's BMI trends move towards an overweight or obesity condition. If the WTA 77 discovers after acquiring a certain number of anthropometry measurements that the person is developing an overweight or obesity condition or is becoming overweight or obese, the module sends a warning message (e.g., Special Overweight or Obesity Signal—S.O.S.) to a person at the discretion of a person who is becoming overweight or obese based upon the LoTOPS service.

After the measurements of weight and height have been completed, the HEWENS device 80 automatically sends the collected data to the TOPS service 30 through a data transmission medium such as a local network or Internet. The HEWENS devices 80 can be purchased by individual users or they can be prescribed by doctor's participating in the HOPM module. Once the information is received and analyzed by the TOPS service 30, an appropriate warning is issued to an individual's healthcare professional if an overweight or obesity condition is predicted. TOPS 30 consists of a client database (CD) 11 and a Weight Trend Analyzer (WTA) 16. The client database automatically collects the name, age, sex, weight, height, and other information of the patient by HEWENS devices 80 through network service 60. The WTA 16 has in its memory a recommended weight for the patient depending on age, sex, and height of the patient. WTA 16 receives the current weight of the person from the CD 11 and creates a graph of the person's weight progress and compares it to a recommended weight progress graph. The WTA 16 then determines if the person's weight trends move towards an overweight or obesity condition. If the WTA 16 discovers that the person is becoming overweight or obese, the module sends a warning message to a person and/or to a health care provider office 70 at the discretion of a person.

Figure 10:
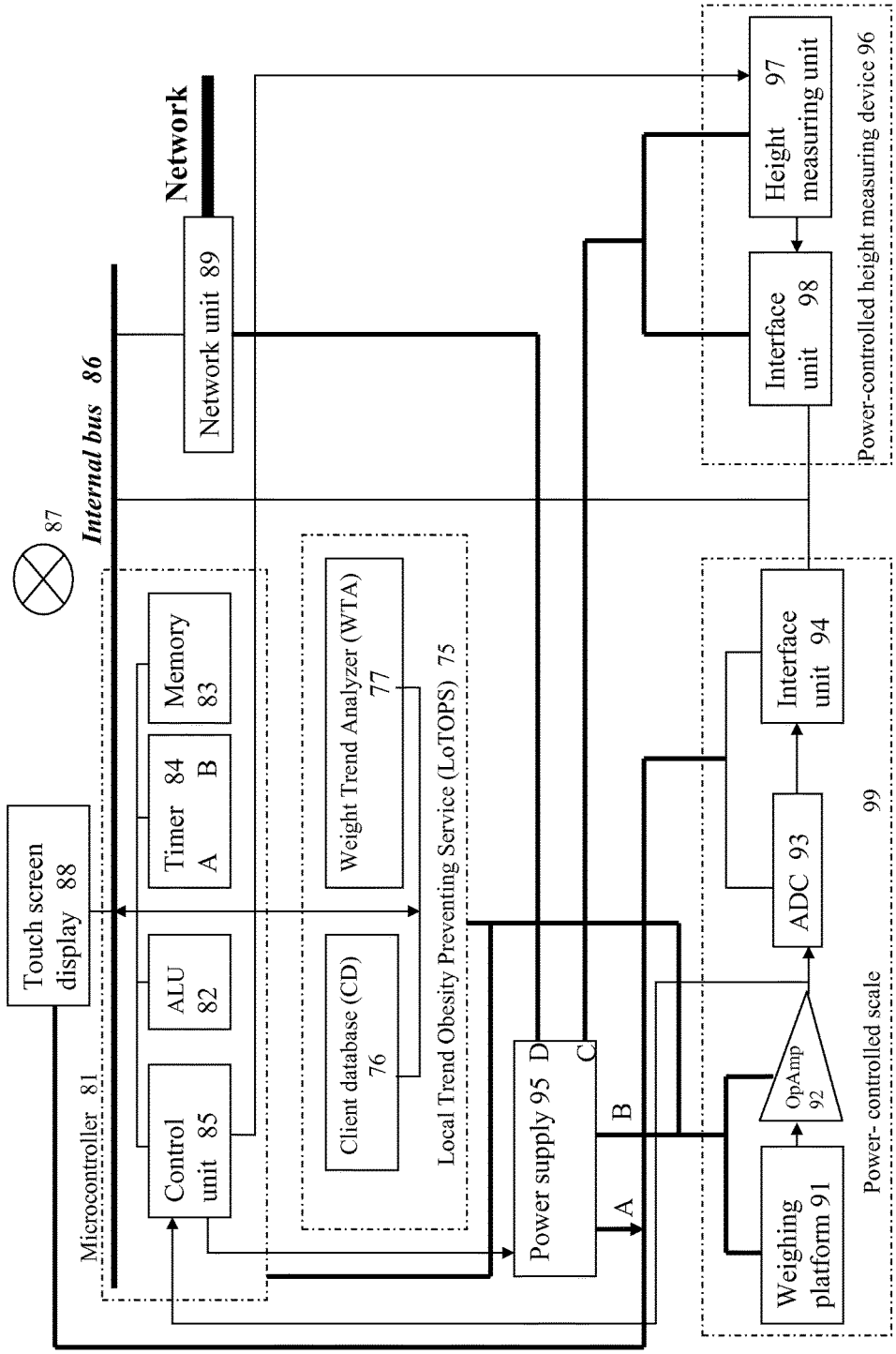
FIG. 10 is a block diagram of a height and weight news sender (HEWENS)

FIG. 10 shows a block diagram of the Height and Weight News Sender (HEWENS) 80 that may include a microcontroller 81, a touch screen display 88, a network unit 89, a Local Trend Obesity Preventing Service (LoTOPS) 75, a power-controlled scale 99, a voltage-controlled power supply 95, and a power-controlled height measuring device 96. The type of display and its existence in a HEWENS structure 80 depends on the user's requirements. The following description is related to a touch screen type of a display-keyboard unit 88. Microcontroller 81, in turn, consists of an arithmetic-logic unit 82, a memory 83, a timer 84, and a control unit 85. LoTOPS 75 consists of a client database (CD) 76 and a Weight Trend Analyzer (WTA) 77. Each HEWENS 80 has Internet address of the trend overweight and obesity preventing service (TOPS 30) for communication via a network service or communications network 60. When the owner or user of the HEWENS unit 80, who appears to be a potential patient, powers up the HEWENS unit 80, for example at home, the touch screen display 88, the network unit 89, the power-controlled scale 99, and the power-controlled height measuring device 96 are all supplied by the power supply unit 95 through its terminals A, C and D. The power-controlled height measuring unit device 96 includes a height measuring unit 97 and an interface unit 98. The power supply unit 95 may be battery powered or a direct AC connection. Microcontroller 81, Local Trend Obesity Preventing Service 75, weighing platform 91, and Operational Amplifier 92 are supplied by the power supply unit 95 through its terminal B constantly.

Figure 11:
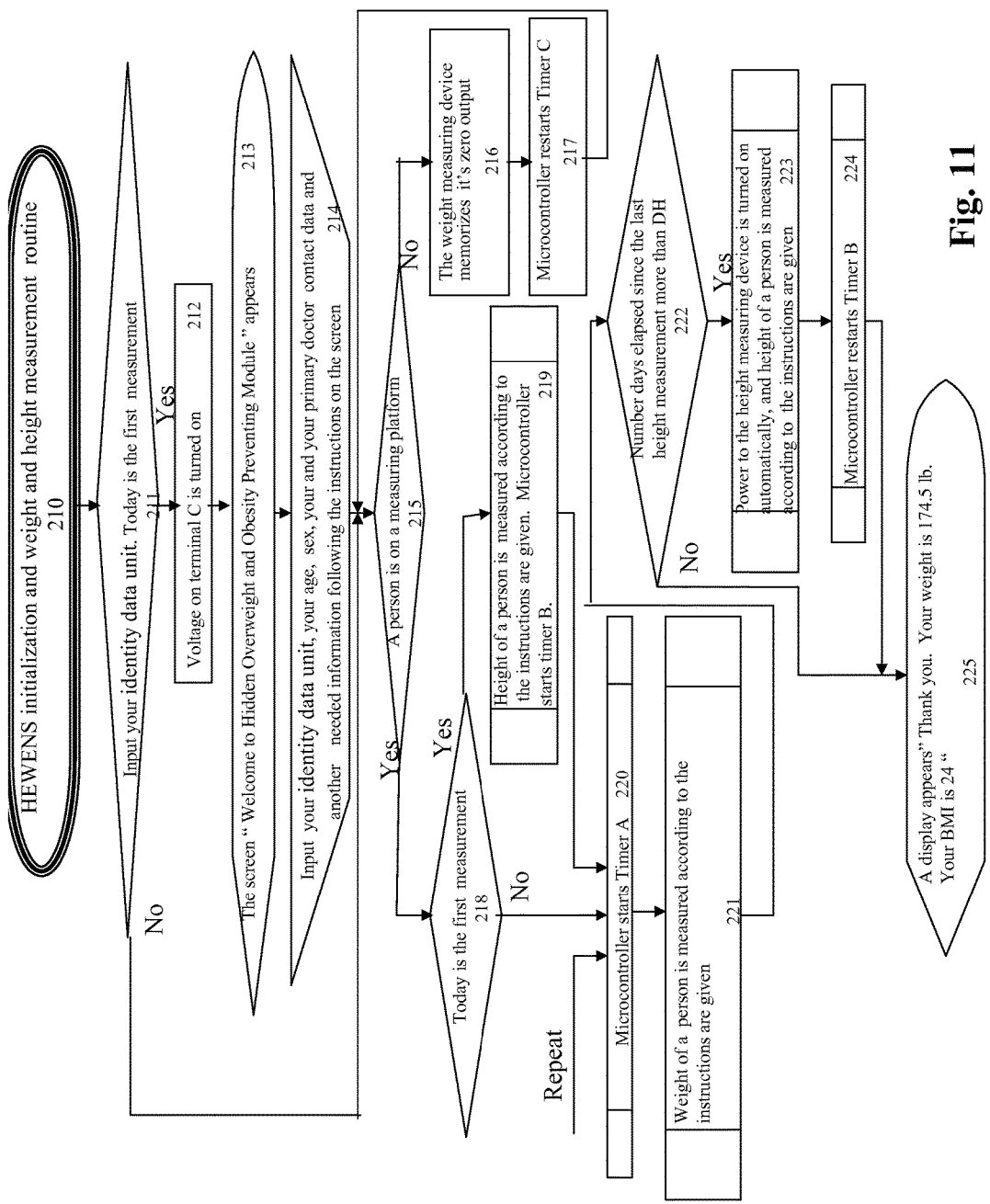
FIG. 11 is a flowchart for the HEWENS initialization and weight and height measurement routine or algorithm resident upon a microprocessor or memory of a module of an exemplary embodiment of the present invention.

FIG. 11 shows a flowchart for HEWENS initialization and weight and height measurement routine 210 or algorithm resident upon a microprocessor or memory of a module of an exemplary embodiment of the present invention. Before it runs the terminal A is powered up. Routine 210 is resident upon the microcontroller of the device. In step 211, the individual is invited to input his/her identity data unit. HEWENS checks if today is the first measurement by the user. If the measurement is the first time at a decision node in step 211, the voltage on terminal C is turned on, in step 212, and the phrase "Welcome to Hidden Overweight and Obesity Preventing Module" appears in step 213. The process flows to step 214 where the individual is invited to input his/her identity data unit, age, sex. The user also asked to input his/her and a health care provider's name, phone and fax numbers and other contact information such as e-mail address. After this initial sequence, the module asks several additional questions, for example, to show or not to show the result of weighing on the screen next time. In step 215, the HEWENS checks to determine if a person is on a measuring platform 91. If a person is not on a measuring platform, then microcontroller 81 memorizes "zero" output of the scale 99 of the HEWENS, in step 216, via the operational amplifier 92, the analog-to-digital converter 93 and the interface unit 94 shown in FIG. 10. In step 217, microcontroller 81 restarts timer C for a time period of several minutes, and continues to monitor a presence of a person on a weighing platform of the scale repeatedly in this time period. When a person steps on measuring platform, the process flows to step 218. HEWENS again checks if today is the first measurement. When HEWENS is turned on for the first time at decision node 218, a height of the person is measured by the height measuring device 96 (shown in FIG. 10) according to the instructions for a height measuring device that is in the use are given in step 219 and microcontroller 81 starts the timer B that will count the number of days (DH) elapsed after the last height reading of the person. The value of DH depends on the age of a person. When HEWENS is not turned on for the first time at decision node 218 or when the height of a person has been measured in step 219, microcontroller 81 starts timer A in step 220 that provides an output signal when 30 minutes have elapsed. Of course, one skilled in the art can determine that other time ranges can be programmed into the unit. After that, the scale 99 weighs the person in step 221. In step 222, microcontroller 81 checks the output of the timer B that counts the number of days elapsed after the last height reading of the person. Every time when the number of days elapsed after the last height reading of the person becomes more than DH, the output of timer B becomes active, terminal C of the power supply is turned on and the height of the person is measured in step 223. Microcontroller 81 restarts timer B in step 224 to start count again the number of days between two consecutive height measurements. The touch screen also shows the weight and BMI of the person in step 225. A patient may be weighed repeatedly in a medical facility by sending a signal Repeat to block 220 by using a pushbutton.

Referring back to FIG. 9 and to FIG. 10, after the HEWENS 80 measures the weight and height of the person, it turns on the voltage on the terminal D of the voltage supply for the network unit 89 and arranges a connection with the network service 60 of the trend overweight and obesity preventing service (TOPS 30) to supply the new data. The HEWENS 80 sends the results of both of the weight and height measurements to the client database 11 of the TOPS 30. and control unit 85 of the microcontroller 81 turns off the output voltage on the terminals A and C of the power supply 95. Terminals A and C supply the power for the touch screen display 88, the height measuring unit 97, the ADC 93, and the interface units 94 and 98 of the power-controlled scale 99 and the height measuring device 96. At this point, the HEWENS 80 starts to work in a hidden mode and only its microcontroller 81, the OP AMP 92, the weight measuring platform 91, LoTOPS 75 and the network unit 89 have voltage supplied from the terminals B and D from the power supply 95. The HEWENS 80 shows that it is in a hidden mode and all is determined to be fine by blinking a green light emitting diode 87 (shown in FIG. 10). The HEWENS 80 uses less power in a hidden mode than in a regular one and stays in this economical mode until a person steps upon the measuring platform the next time. If the message is not able to be sent due to communications problems, the timer A finishes its count, the timer's output becomes active, and HEWENS 80 (shown in FIG. 2) sends a service warning message. Then the control unit 85 of the microcontroller 81 turns off the output voltage on the terminals A, C and D of the power supply 95. When a person steps on the measuring platform the next time, the Op Amp 92 of the scale 99 creates a signal that the control unit 85 sees, and microcontroller 81 triggers multi-channel timer 84, timer A which commences a count. Simultaneously, control unit 85 turns on the output voltage on terminals A and D. The output voltage on terminal C of the power supply 95 is not be turned on because the HEWENS 80 measures the height of a person in DH days. After the scale measures the person's weight, the HEWENS 80 establishes a network connection with the network service 60 and the client database 11 of the TOPS 30. The TOPS 30 receives this data by a message from the HEWENS 80. The voltage is turned off from terminal A, and the HEWENS 80 goes into the hidden mode again. If the message is not able to be sent due to communications problems, the timer A finishes its count, the timer's output becomes active, and the HEWENS 80 sends a service warning message.

Figure 12:
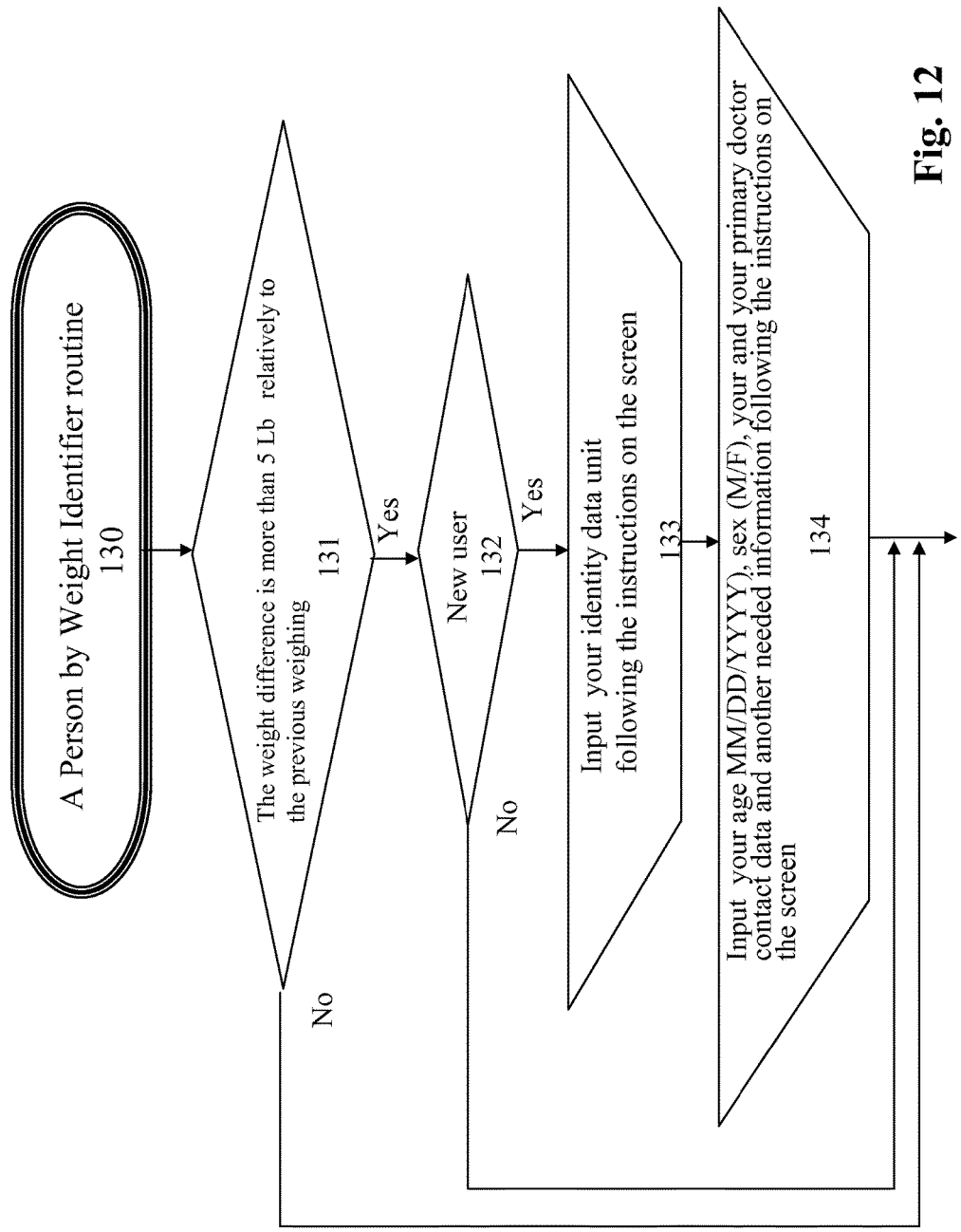
FIG. 12 is a flowchart for a person by weight identifier routine resident upon a microprocessor or memory of a module of an exemplary embodiment of the present invention.

FIG. 12 shows a flowchart of a person by Weight Identifier routine or algorithm 130, which is also resident upon the microcontroller of the device. In every new measurement, a Person by Weight Identifier routine 130 recognizes the owner of the HEWENS 80 by his weight 131. If the weight difference between two consecutive measurements is more than 5 pounds, routine 130 checks if a different person is attempting to use the HEWENS 80, in step 132. If so, the new person or patient is invited to input his/her identity data unit 133. Of course, one skilled in the art can determine that other weight ranges can be programmed into the unit. If it is determined there is a new user, the system asks to input, in step 134, their identity data unit, age, height, sex, and contact information of the person and his/her health care provider. After this initial sequence, the system asks several additional questions, for example, to show or not to show the result of weighing and calculated BMI on the screen. As an alternative, and when the TOPS service is provided as a subscription service each new user may be asked to pay a subscription fee, for example by a credit card, wherein the credit card information is also inputted in the HEWENS 80. The HOPM uses a Weight Trend Analyzer routine 240 (shown in FIG. 4). After HEWENS 80 sends each new message consisting of a weight and if applicable height data to the TOPS 30, the WTA collects measurements of weight and height of a person and estimates a probability of a person's obesity in next several months or later. Of course, the periods mentioned above may be greater or less than the aforementioned values. Thus, the exemplary embodiments of the present invention provide a hidden overweight and obesity preventing module and method that may predict an obesity trend or lack thereof.

In still yet another alternative exemplary embodiment the HEWENS weight and height sender of the HOPM module may be accomplished as a Comprehensive Anthropometry Apparatus (COMANTUS) that automatically performs the following steps/functions: read person's identity data by employing a bar code scanner and/or a fingerprint reader; measure the person's weight and height (if it is the time to measure a height) when the person steps onto a measuring platform for weight and height measuring; provide audio communication with the person; and provide the results of the measurements in the form of weight, height, and BMI, and transmit the result of measurements to the TOPS 30 via data transfer means, e.g., local network, Internet, or wireless communications, etc.

Figure 13:
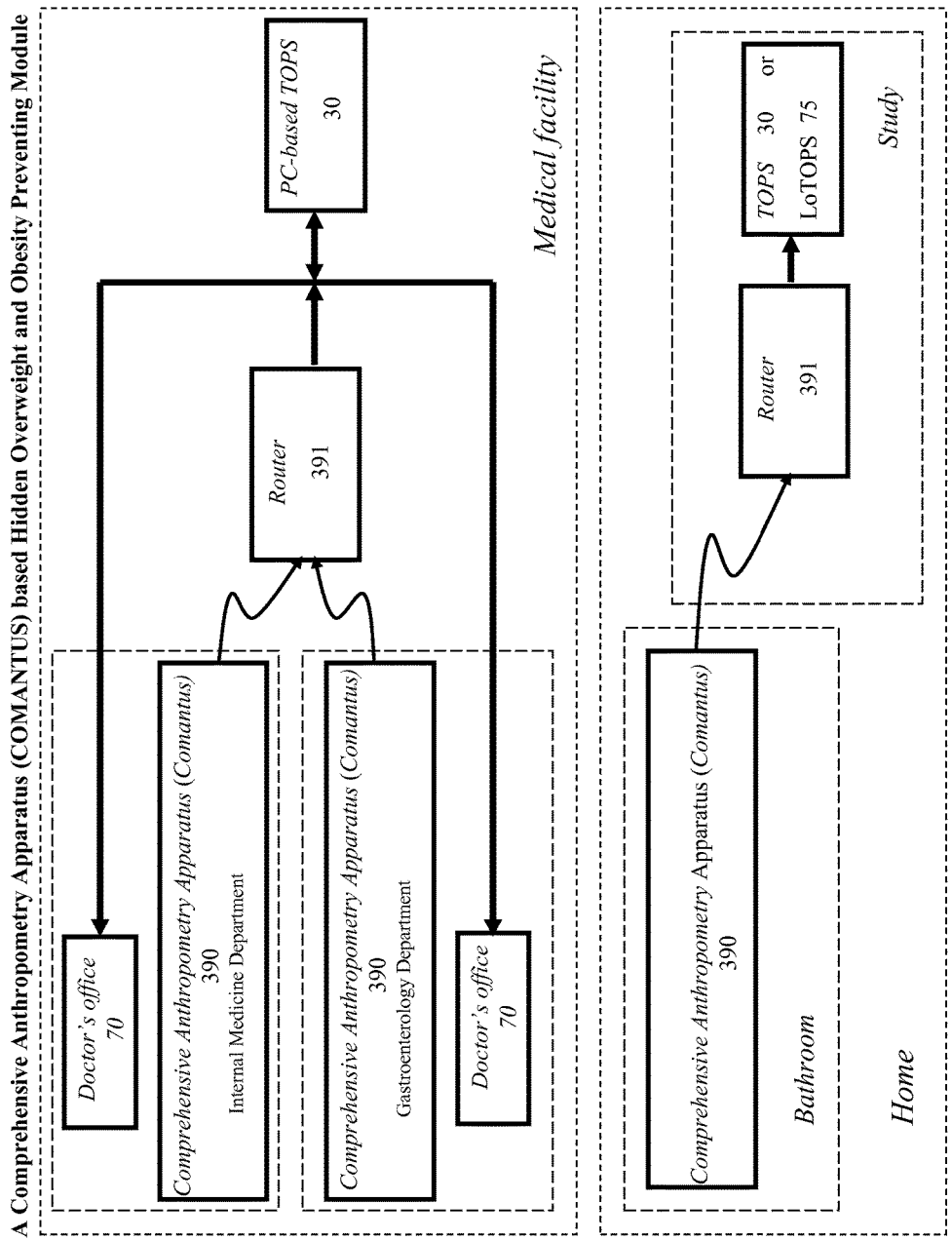
FIG. 13 is a block diagram of a Comprehensive Anthropometry Apparatus (COMANTUS) based Hidden Overweight and Obesity Preventing Module (HOPS)

FIG. 13 shows a block diagram of the Comprehensive Anthropometry Apparatus (COMANTUS) based Hidden Overweight and Obesity Preventing Module (HOPM) structure according to an exemplary embodiment of the present disclosure that may be employed in a medical facility or at home. The home HOPM module may include at least one Comprehensive Anthropometry Apparatus (COMANTUS) 390 located in any room (e.g. in a bathroom). COMANTUS 390 collects weight and height measurements of a person when he/she steps onto a measuring platform and transmits this data wirelessly to LoTOPS 75 of a HEWENS 80 or TOPS 30 located in another room (e.g. in a study) through a router 391. LoTOPS 75 or TOPS 30 processes this information as was described above. HOPM module located in a medical facility (see FIG. 13) may include a plurality of COMANTUS 390 located in any department (e.g. in a Internal Medicine and/or Gastroenterology Departments). Each COMANTUS 390 collects weight and height measurements of a patient in its Department when he/she steps onto a measuring platform. COMANTUS 390 transmits this data wirelessly to TOPS 30 located in any room of the medical facility through a router 391. After the data has been processed in LoTOPS 75 or TOPS 30, the WTA 77 of the LoTOPS 75 or WTA 16 of the TOPS 30 accordingly then determines if the patient's weight trends move towards an overweight or obesity condition. If the WTA 77 of the LoTOPS 75 discovers that the patient is becoming overweight or obese, the module sends a warning message to a person at his/her discretion. If the WTA 16 of TOPS 30 discovers that the patient is becoming overweight or obese, the module sends a warning message at the person's discretion to a health care provider in office 70.

Figure 14:
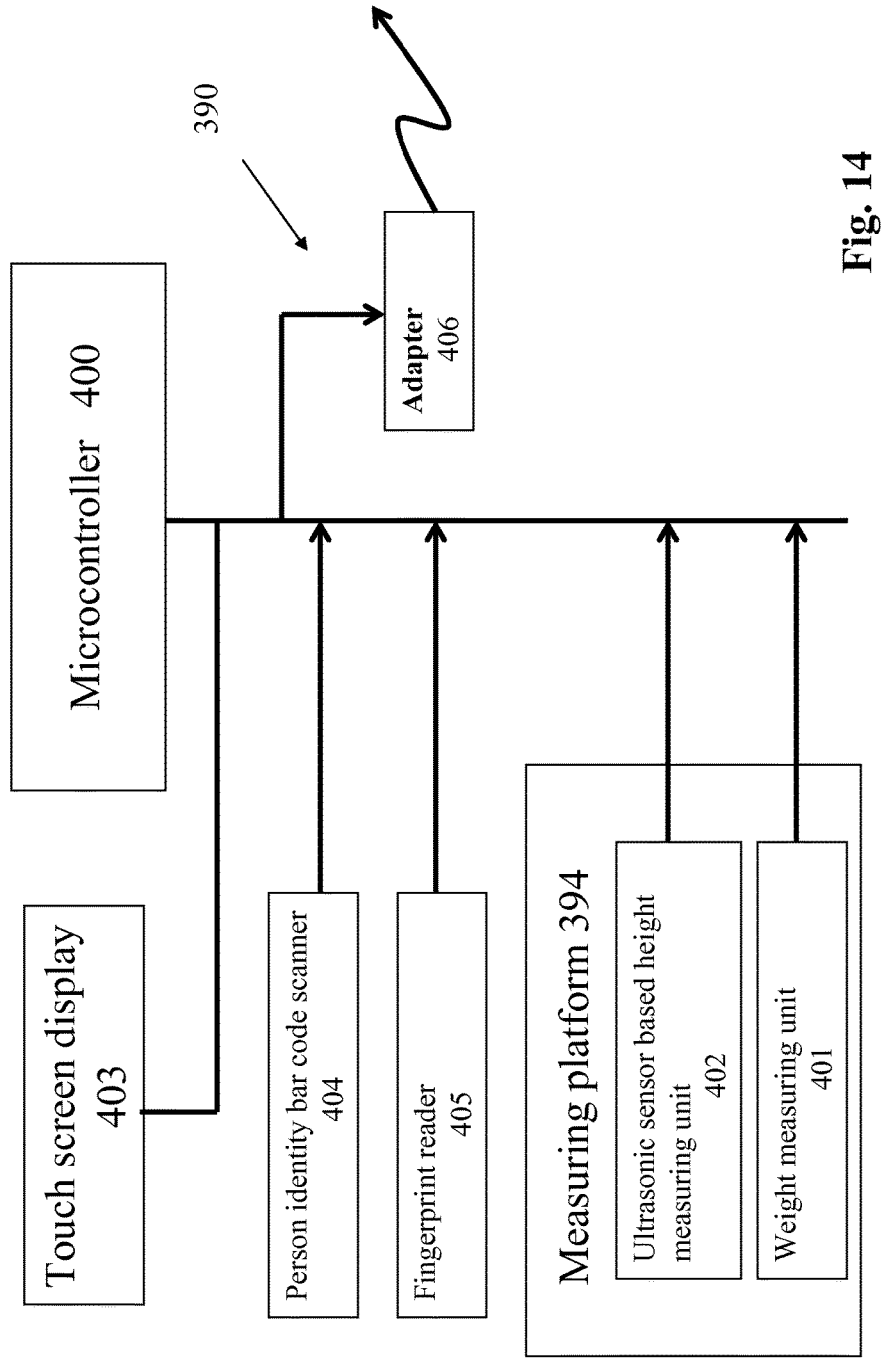
FIG. 14 is a block diagram of the Comprehensive Anthropometry Apparatus.

FIG. 14 shows a block diagram of the Comprehensive Anthropometry Apparatus (COMANTUS) 390 according to an exemplary embodiment of the present invention that includes a microcontroller 400, a touch screen display 403, an adapter 406, a measuring platform 394, person identity bar code scanner unit 404, and a fingerprint reader unit 405. The measuring platform 394 includes a weight measuring unit 401 and ultrasonic sensor based height measuring unit 402. In one embodiment, adapter 406 is a communication device of a COMANTUS that transmits data collected by the COMANTUS (e.g., weight and height measurements) to a Hidden Overweight and Obesity Preventing Module through for example a router 391 (see FIG. 13). In another exemplary embodiment, the router may provide communication services for several COMANTUSes through their adapters.

Another exemplary embodiment of the present invention is that improves the accuracy of an ultrasonic sensor height measurement of a person by use of a disk that has a flat outside surface and oval inside surface and is secured on the top of the head of the person during the height measurement.

Of course, one skilled in the art can determine that other types of a person identity scanner unit and a height measuring unit can be used in the Comprehensive Anthropometry Apparatus 390.

Figure 15:
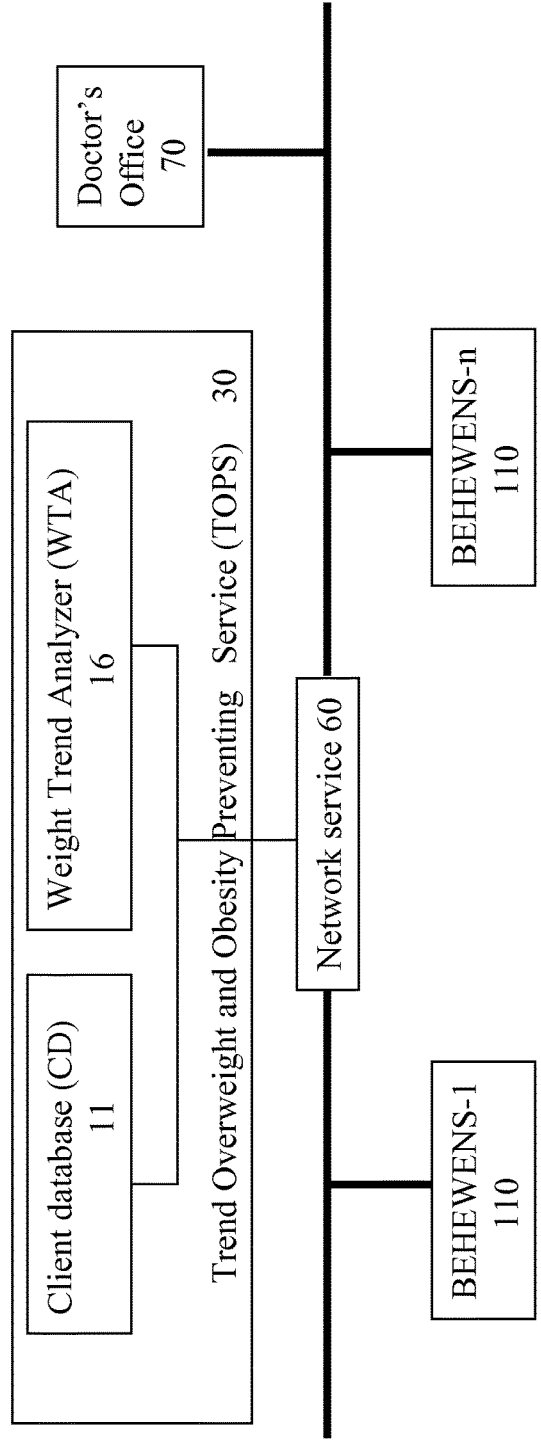
FIG. 15 is a block diagram of a Resting Overweight and Obesity Preventing Module (ROPM)

FIG. 15 shows a block diagram of the Resting Overweight and Obesity Preventing Module (ROPM) structure according to an exemplary embodiment of the present disclosure. The ROPM module may include a plurality of Bed Height and Weight News Senders (BEHEWENS) 110 apparatuses for data collection and a one-way automatic data transmission (e.g., via data transfer means, e.g., local network, Internet, or wireless communications, etc.) to a main data service. The structure of the ROPM is similar to the HOPM, but the ROPM employs another type of Height and Weight News Senders than does the HOPM. To acquire weight measurements of an individual, the HOPM uses a weighing platform of a scale on a floor as an individual steps onto a scale when the individual goes to (from) a bed at night (in the morning). To acquire weight measurements of an individual, the ROPM uses weight cells or a scale weighing platform installed in a bed, chair, recliner, etc. where the individual rests at home every night or where a medical patient rests for a long period of time in a hospital or other medical facility because of illness. When ROPM collects weight measurements of a person in order to forecast a future trend of weight progress, it employs a Weight Trend Analyzer to define a probability of an obesity condition of a person in a short period of time in the future. After diagnosing a possible overweight or obesity situation of a person in the future, the ROPM sends warning to a person's or his/her children's health care professional at the person's discretion. Thus, health care professional has an opportunity to start treatment for this person before any serious mental and body changes of a person take place.

The Module communicates with a TOPS 30, which may be a personal computer (PC). The main objective of this service is to collect the weight and height data automatically received from patients through a plurality of the BEHEWENS 110 using a data transfer means such as a network service 60 configured to receive and disperse the collected information. The BEHEWENS 110 is an automatic device that is activated by an individual when he/she lies upon a weight and height measuring device of an individual resting place.

After the required measurements of weight and height (once in a while) have been completed, they are sent to the small Local Trend Obesity Preventing Service (LoTOPS) 75 of the BEHEWENS device 110 through an internal bus. The Local Trend Obesity Preventing Service (LoTOPS) 75 serves to BEHEWENS device 110 users only and depends on the preferences of the users of the BEHEWENS to monitor their weight trend at home or in medical facility or not to monitor.

LoTOPS 75 consists of a client database (CD) 76 and a Weight Trend Analyzer (WTA) 77. The client database automatically collects the name, age, sex, weight, height, and other information of the person. The WTA 77 has in its memory a recommended BMI for the person depending on age, sex, and height of the person. WTA 77 receives the current weight and height of the person from the CD 76 and creates a graph of the person's BMI progress and compares it to a recommended BMI progress graph. The WTA 77 then determines if the person's BMI trends move towards an overweight or obesity condition. If the WTA 77 discovers after acquiring a certain number of anthropology measurements that the person is becoming overweight or obese, the module sends a warning message to a person at the discretion of a person. After the required measurements of weight and height have been completed, the BEHEWENS 110 automatically sends the collected data to the TOPS 30 through a data transmission medium. The BEHEWENS 110 can be purchased by individual users or they can be prescribed by doctor's participating in the ROPM module. Once the information is received and analyzed by the TOPS 30, an appropriate warning is issued to a person and/or to person's health care professional if an obesity condition is predicted. TOPS 30 consists of a client database (CD) 11 and WTA 16. The CD 11 and the WTA 16 have been described previously with respect to FIG. 9. These functions of the ROPM are similar to the functions of the HOPM described in FIG. 9.

Figure 16:
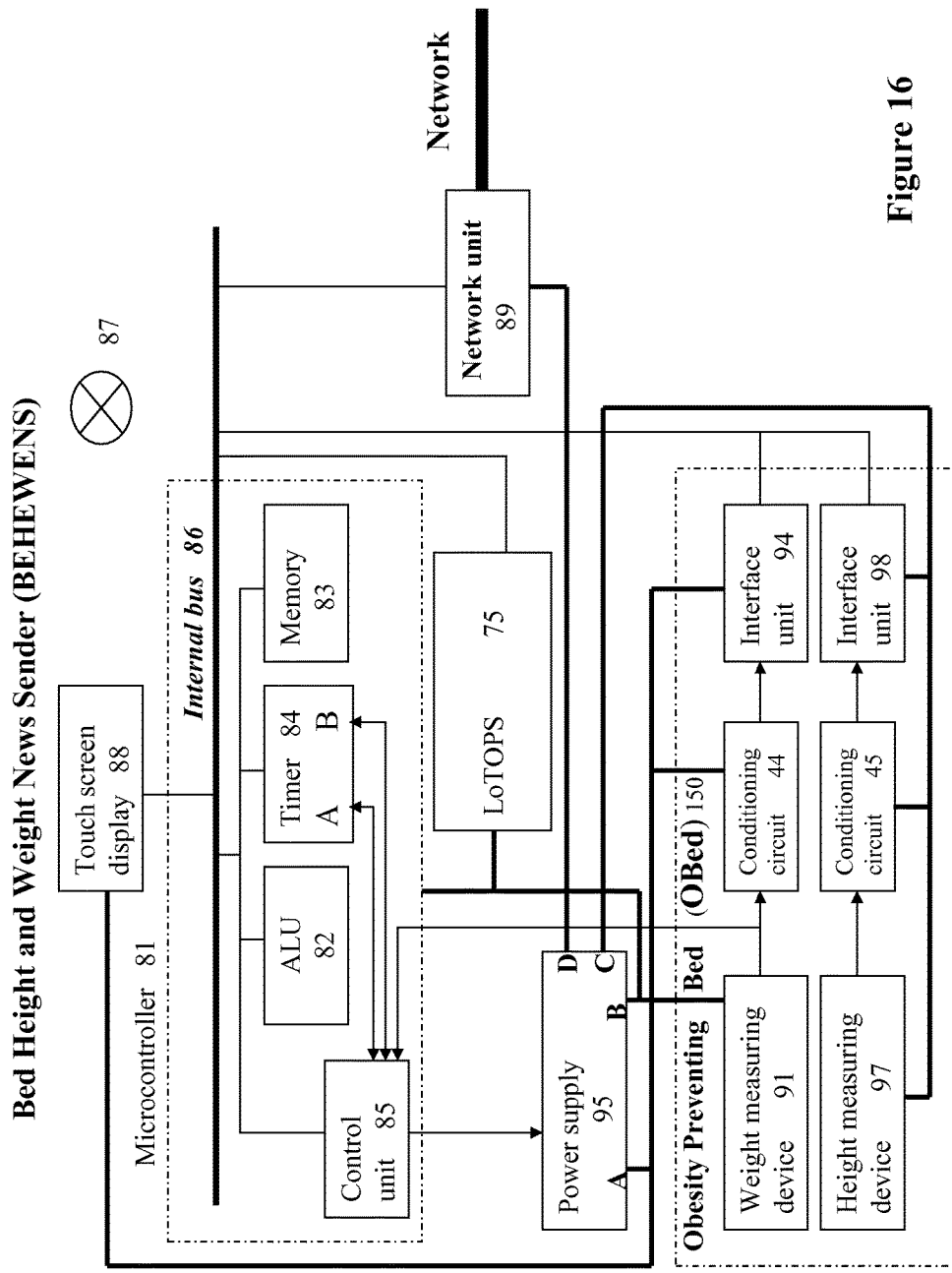
FIG. 16 is a block diagram of a Bed Height and Weight News Sender (BEHEWENS)

FIG. 16 shows a block diagram of the BEHEWENS 110 according to an exemplary embodiment of the present invention that may include a microcontroller 81, a touch screen display 88, a network unit 89, a Local Trend Obesity Preventing Service (LoTOPS) 75, a voltage-controlled power supply 95, an Obesity Preventing Bed (OBed) 150, and a light emitting diode 87. The OBed 150 includes a power-controlled weight measuring device 91, a power-controlled height measuring device 97, conditioning circuits 44 and 45, and interface units 94 and 98. The analog-to-digital converters are included into conditioning circuits. The following description is related to a touch screen type of a display-keyboard unit 88. Microcontroller 81, in turn, consists of an arithmetic-logic unit 82, a memory 83, a timer 84, a control unit 85, and an internal bus 86. LoTOPS 75 of BEHEWENS 110 has the same structure as LoTOPS 75 of HEWENS 80 and consists of a client database (CD) 76 and a Weight Trend Analyzer (WTA) 77. Each BEHEWENS 110 has an address of the TOPS 30 for communication via a network or communications network. When the owner or user of the BEHEWENS 110, who appears to be a potential patient, powers up the BEHEWENS 110, the touch screen display 88, the network unit 89, the conditioning circuits 44 and 45, the interface units 94 and 98, and the power-controlled height measuring device 97 are supplied power by the power supply 95 through its terminals A, C, and D. The power supply unit 95 may be battery powered or a direct AC connection. The microcontroller 81, Local Trend Obesity Preventing Service 75, and the power-controlled weight measuring device 91 are supplied power by the power supply unit 95 through its terminal B.

Figure 17:
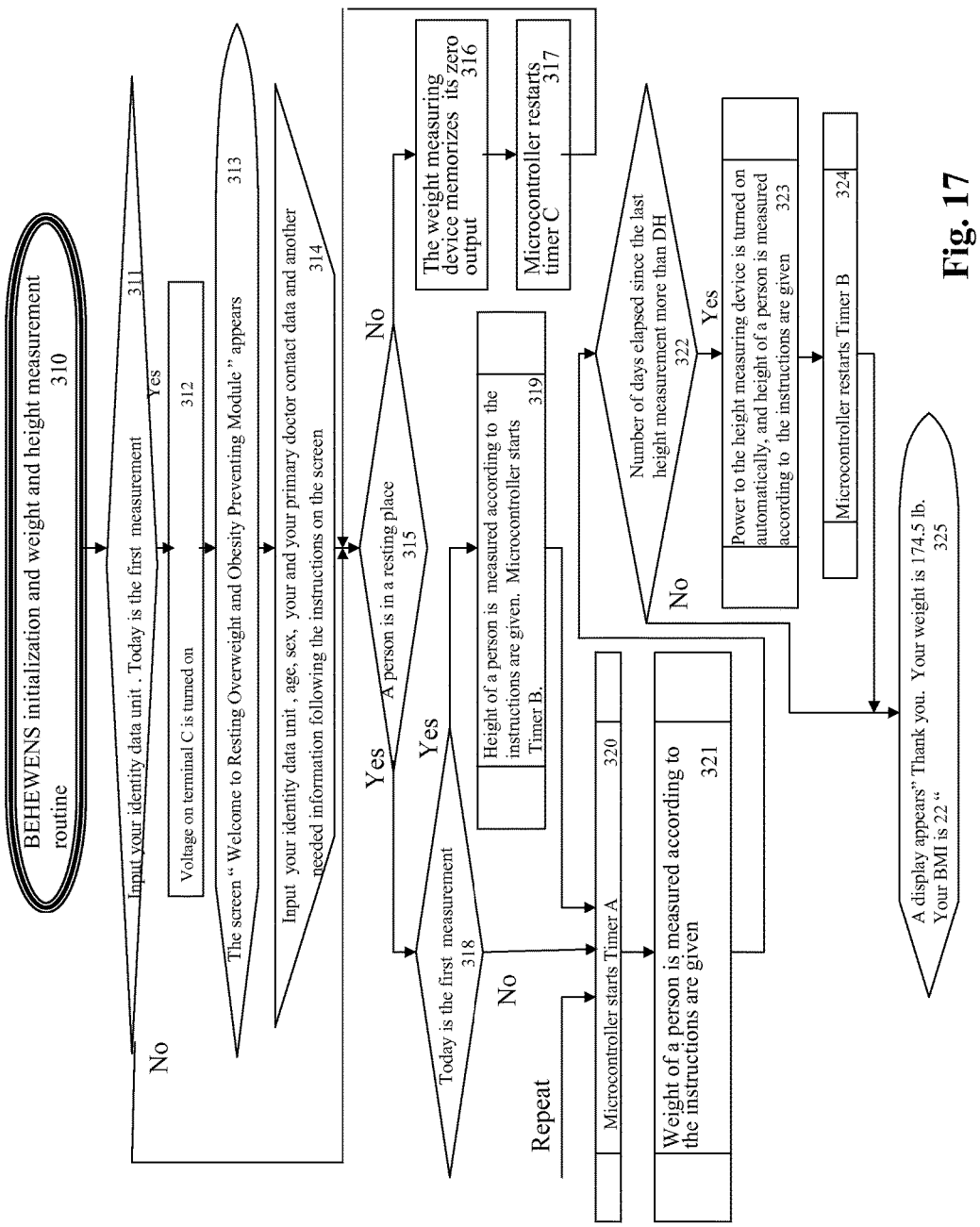
FIG. 17 is a flowchart for the BEHEWENS initialization and weight and height measurement routine or algorithm resident upon a microprocessor or memory of a module of an exemplary embodiment of the present invention.

FIG. 17 shows a flowchart for BEHEWENS initialization and weight and height measurement routine 310. Before it runs, the terminal A is powered up. Routine 310 is resident upon the microcontroller of the device. In step 311 the person is invited to input his/her identity data unit. BEHEWENS checks to determine if today is the first measurement by the user. If the measurement is the first time at decision node 311, the voltage on terminal C is turned on, in step 312, and the phrase "Welcome to Resting Overweight and Obesity Preventing Module" appears, in step 313. Then in step 314, the individual is invited to input his/her identity data unit, age, sex. The user also is asked to input his/her and a health care professional's name and contact data. After this initial sequence, the module asks several additional questions, for example, to show or not to show the result of weighing on the screen.

Figure 18:
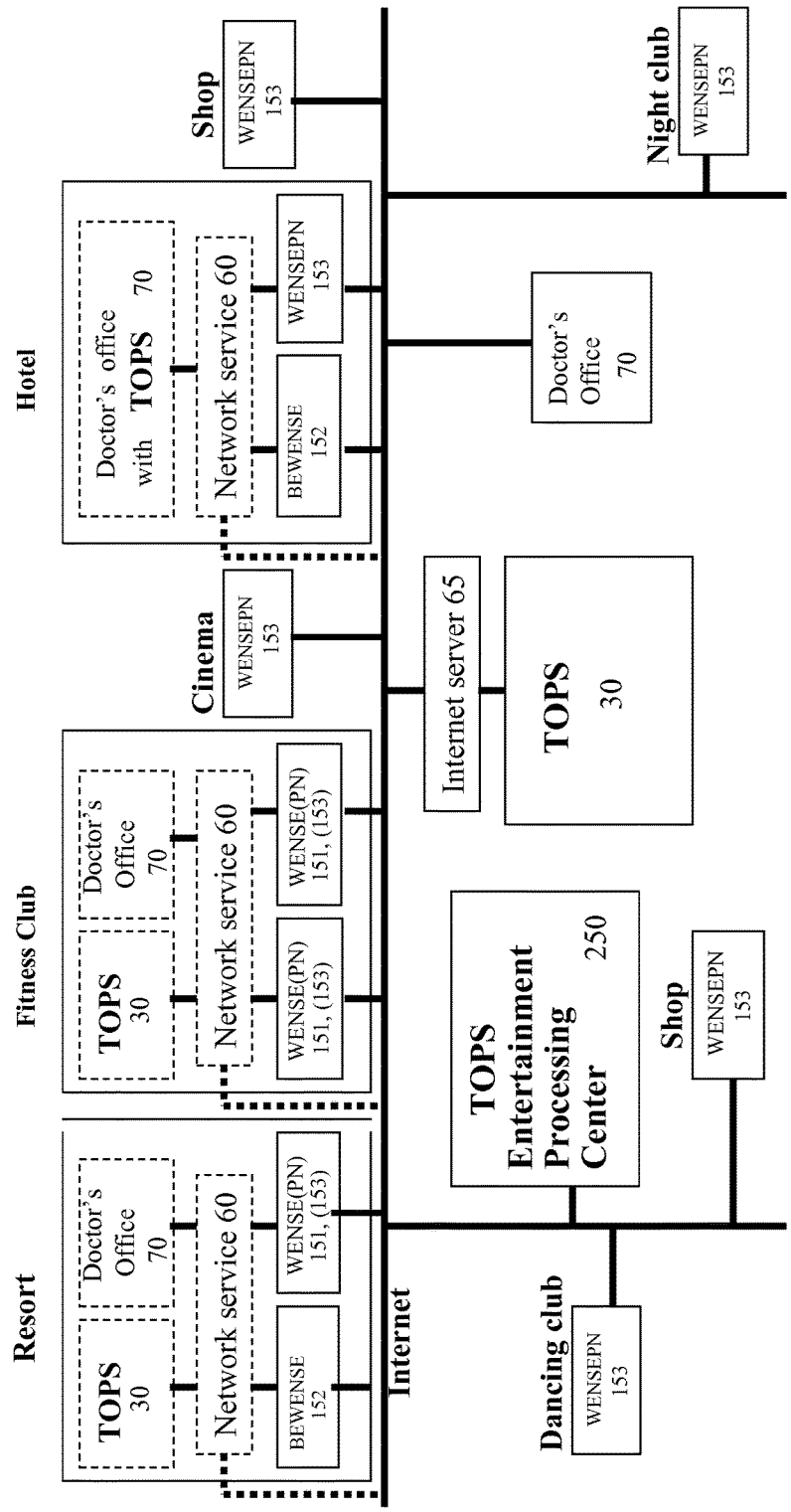
FIG. 18 is a block diagram of the Entertainment Overweight and Obesity Preventing Modules (EOPM) structure.

When the TOPS 30 is provided as a subscription service each new user may be asked to pay a subscription fee for example by a credit card, wherein the credit card information is also inputted in BEHEWENS 110. In step 315, the BEHEWENS 110 checks to determine if a person is in a resting place. If a person is not in Obesity Preventing Bed 150, microcontroller 81 memorizes "zero" output of the weight measuring device 91 of the BEHEWENS, in step 316, through conditioning circuit 44 and interface unit 94 (shown in FIG. 16). In step 317, microcontroller 81 restarts timer C for a time period of several minutes, and continues to monitor a presence of a person in Obesity Preventing Bed 150. When a person is laying upon Obesity Preventing Bed 150, the process flows to step to 318. The BEHEWENS again checks to determine if today is the first measurement of the user. When the BEHEWENS is turned on for the first time at decision node 318, a height of the person is measured by the height measuring device 97 located in Obesity Preventing Bed 150 according to the instructions for a height measuring device, in step 319, and the microcontroller 81 starts timer B that counts the number of days elapsed after the last height reading of the user. When the BEHEWENS is not turned on for the first time at decision node 318 or when the height of the person has been measured in step 319, the microcontroller 81 starts timer A, in step 320 that provides an output signal when 30 minutes have elapsed. Of course, one skilled in the art will recognize that other time ranges can be programmed into the unit. Then, the weight measuring device 91 located in the Obesity Preventing Bed 150 weighs the person, in step 321. It is preferred in order to obtain the best results to measure weight of the person at the same time of day (e.g., at night when a person goes to bed with minimal clothes on). Microcontroller 81 then checks an output of the timer B that counts the number of days elapsed after the last height reading of the person was measured, in step 322. Every time when the number of days elapsed after the last height reading of the patient becomes more than DH, the output of timer B becomes active, terminal C of the power supply is turned on and the height of the person is measured in step 323. Microcontroller 81 restarts timer B in step 324 to count the next portion of number of days between two consecutive height measurements. In step 325, the touch screen also shows the weight and BMI of the person. A patient may be weighed repeatedly in a medical facility by sending a signal Repeat to block 320 by using a pushbutton. FIG. 18 shows a block diagram of the Entertainment Overweight and Obesity Preventing Module (EOPM) structure. The EOPM modules employ at least one WENSE 151 (Weight News Sender Entertainment) and/or at least one BEWENSE 152 (Bed Weight News Sender Entertainment) for data collection and automatic communication (via data transfer means, e.g., local network, Internet, or wireless communications, etc.) with a trend obesity preventing service TOPS 30. The module employs a TOPS 30 or TOPS Entertainment Processing Center 250 and interacts with other modules. The primary objective of TOPS 30 is to collect the weight and height data automatically received from persons through a plurality of the WENSE 151 and BEWENSE 152 by using a data transfer means such as a network service 60 configured to receive and disperse the collected information. The WENSE 151 device is an automatic Weight News Sender that is activated by an individual when he/she steps onto a weighing platform of a scale in a resort, hotel, etc. The structure of the WENSE 150 is very similar to the HEWENS 80. The BEWENSE 152 device is an automatic Bed Weight News Sender that is activated by an individual when he/she is laying upon a weight measuring device in an individual's Overweight Preventing Bed 150 in a resort, hotel, etc. A height data is collected by WENSE 151 or BEWENSE 152 from user during a login procedure and once in a while. After the required measurements of weight have been completed by WENSE 151 or by BEWENSE 152, they are sent to the appropriate Local Trend Obesity Preventing Service (LoTOPS) 75 of the WENSE 151 or BEWENSE 152 through an internal bus. LoTOPS 75 consists of a client database (CD) 76 and a Weight Trend Analyzer (WTA) 77. The client database automatically collects the name, age, sex, weight, height, and other information of the person. The WTA 77 has in its memory a recommended BMI for the person depending on age, sex, and height of the person. WTA 77 receives the current weight and height of the person from the CD 76 and creates a graph of the person's BMI progress and compares it to a recommended BMI progress graph. The WTA 77 then determines if the person's BMI trends move towards an overweight or obesity condition. If the WTA 77 discovers after acquiring a certain number of anthropology measurements that the person is becoming overweight or obese, the module sends a warning message to a person at the discretion of a person.

Once the measurements of weight have been completed, the WENSE 151 or BEWENSE 152 automatically sends the collected data to the TOPS service 30 through a data transmission medium such as a local network or Internet. After the information is received and analyzed by the TOPS service 30, an appropriate warning is issued at the discretion of a person to a person's healthcare professional if an overweight or obesity condition is forecasted. If a resort or hotel does not have a data transmission medium such as a local network, the WENSE 151 or BEWENSE 152 directly sends the collected data to the TOPS 30 of the EOPM through the Internet. The TOPS of the EOPM may be located as a separate service TOPS 30 or may be included into entertainment processing center 250. For the users WENSE 151 or BEWENSE 152 who employs GOPS only several times and for a short period of time, WENSE 151 or BEWENSE 152 may show a fitness screen, weight graph, and any popular text.

Figure 19:
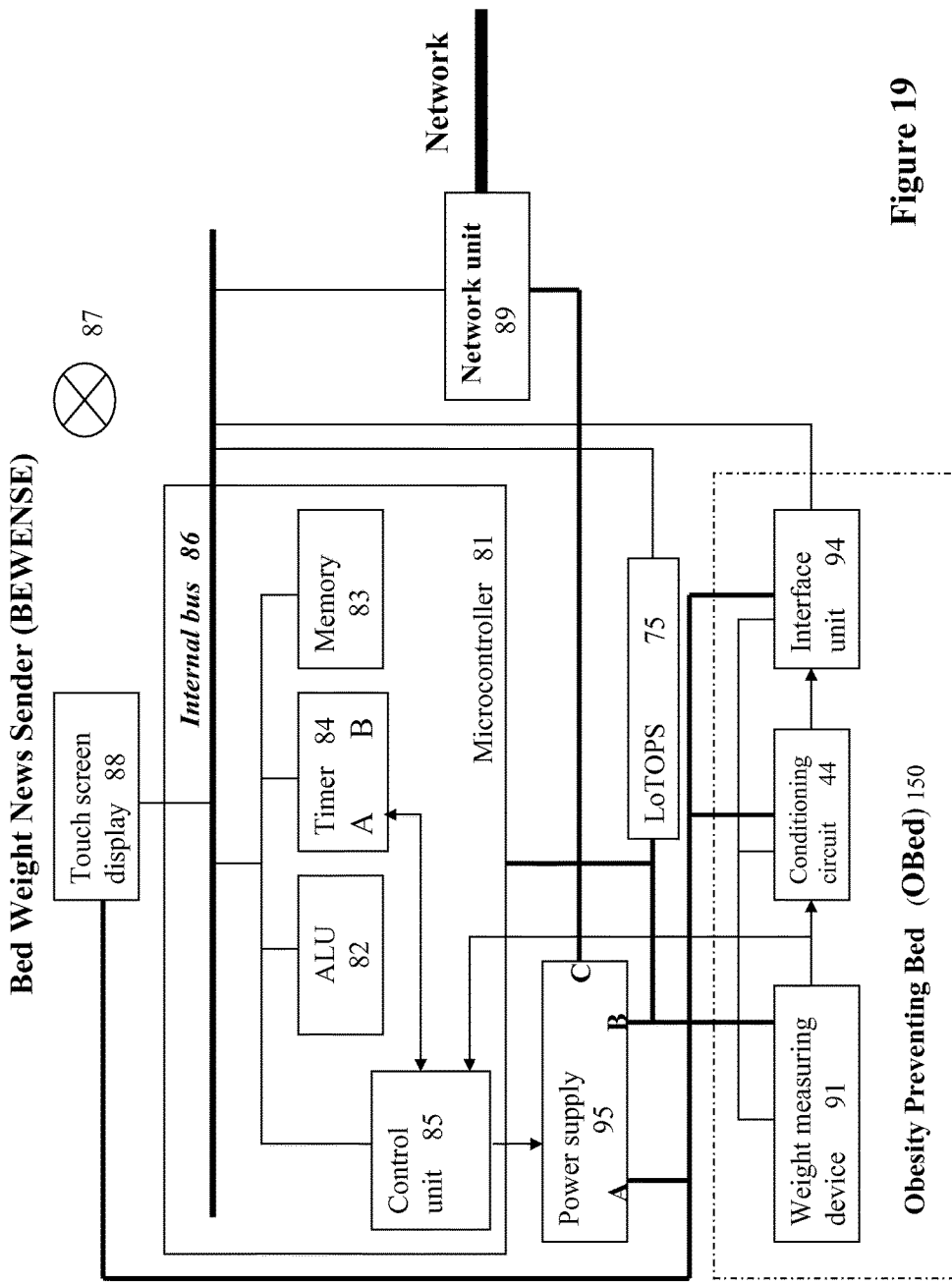
FIG. 19 is a block diagram of a Bed Weight News Sender (BEWENSE)

FIG. 19 shows a block diagram of the BEWENSE 152 according to an exemplary embodiment of the present invention that includes of a microcontroller 81, a touch screen display 88, a local Trend Obesity Preventing Service (LoTOPS) 75, a network unit 89, a voltage-controlled power supply 95, an Obesity Preventing Bed (OBed) 150, and a light emitting diode 87. The OBed 150 includes a weight measuring device 91, a conditioning circuit 44, a interface unit 94 and has its own microcontroller and internal bus. The analog-to-digital converter is included into the conditioning circuit. The following description is related to a touch screen type of a display-keyboard unit 88. The microcontroller 81, in turn, consists of an arithmetic-logic unit 82, a memory 83, a timer 84, a control unit 85, and an internal bus 86. When the owner or user of the BEWENSE 152, who appears to be a potential patient, powers up the BEWENSE 152, the touch screen display 88, the network unit 89, the conditioning circuit 44, and the interface unit 94 are to be supplied with power by the power supply 95 through its terminals A and C. The power supply 95 may be battery powered or a direct AC connection. The microcontroller 81, Local Trend Obesity Preventing Service (LoTOPS) 75, and the power-controlled weight measuring device 91 are supplied power by the power supply unit 95 through its terminal B.

Figure 20:
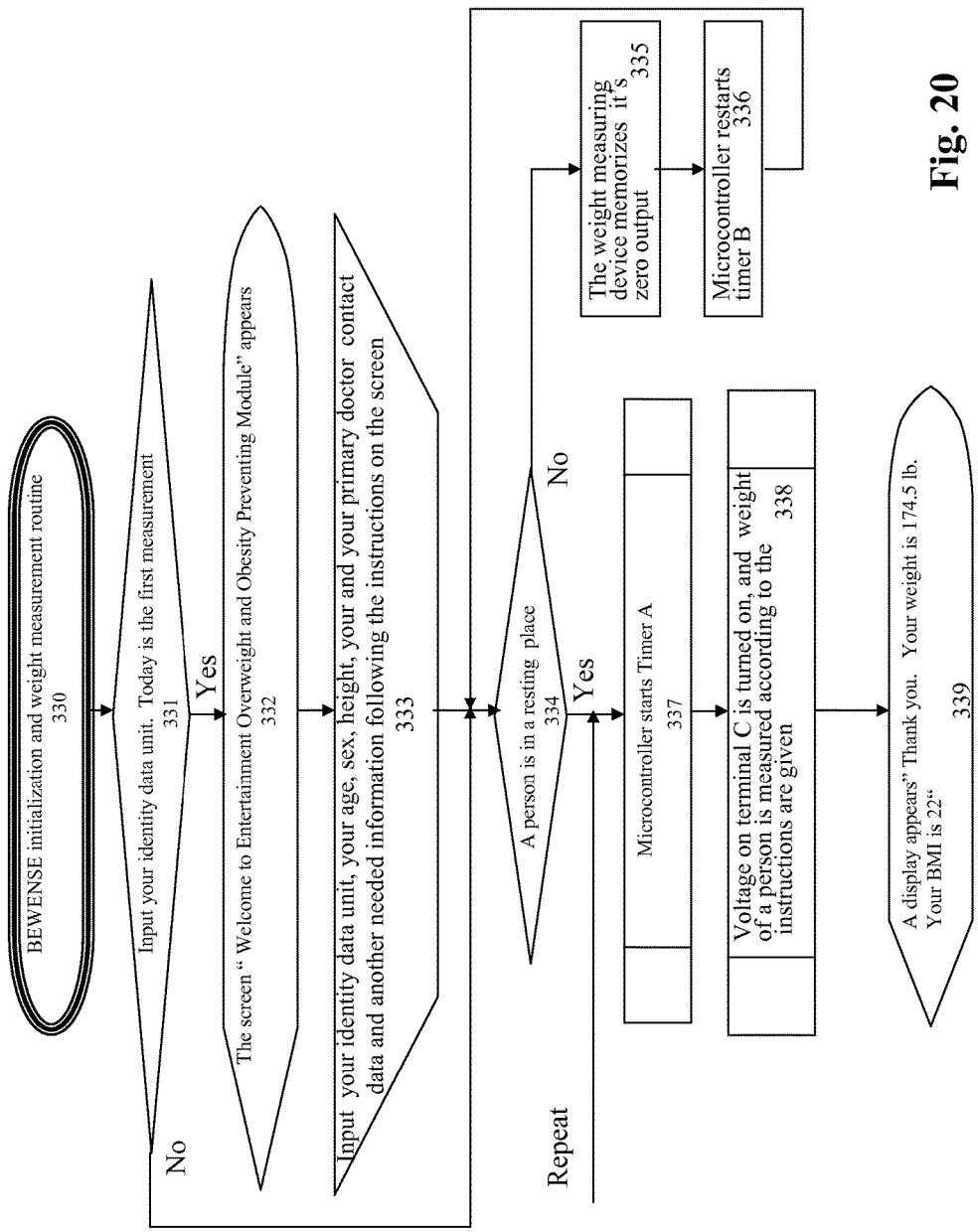
FIG. 20 is a flowchart for the BEWENSE initialization and weight measurement routine or algorithm resident upon a microprocessor or memory of a module of an exemplary embodiment of the present invention.

FIG. 20 shows a flowchart for BEWENSE initialization and weight measurement routine 330. Before it runs, the terminal A of the power supply 95 is powered up. Routine 330 is resident upon the microcontroller of the device. In step 331 a person is invited to input his/her identity data unit. BEWENSE checks in 331 to determine if today is the first measurement of the user. If the measurement is the first time at decision node 331, the phrase "Welcome to Entertainment Overweight and Obesity Preventing Module" appears in step 332. In step 333, the individual is invited to input his/her identity data unit, age, sex, height. The user also is asked to input his/her and a health care provider's contact information. After this initial sequence, the module asks several additional questions, for example, to show or not to show the result of weighing on the screen next time. In step 334, the BEWENSE checks if a person is in a resting place. If a person is not in Obesity Preventing Bed 150, the microcontroller 81 memorizes "zero" output of the weight-measuring device 91 of the BEWENSE, in step 335, through the conditioning circuit 44 and interface unit 94 (shown in FIG. 19). In step 336, the microcontroller 81 restarts timer B for a time period of several minutes, and continues to monitor a presence of a person in Obesity Preventing Bed 150 repeatedly in this time period. When a person is laying upon Obesity Preventing Bed 150, the process flows to step 337. When BEWENSE is not turned on for the first time at decision node 331, the microcontroller 81 starts timer A, in step 337, which provides an output signal when 3 minutes of time have elapsed. Of course, one skilled in the art can recognize that other time ranges can be programmed into the unit. After that, the voltage on terminal C is turned on and the weight-measuring device 91 located in the Obesity Preventing Bed 150 weighs the person, in step 338. In step 339, the touch screen will also show the weight and BMI of the person. A patient may be weighed repeatedly in a medical facility by sending a signal Repeat to block 337 by using a pushbutton.

In addition and in accordance with another exemplary embodiment of the present invention, the SVOPS, HOPM, ROPM, and EOPM modules are configured with different kind of children's growth charts according to age and sex in the local WTA 76 and in the WTA 16 of GOPS, wherein the information provided by HEWENS, BEHEWENS, WENSE, and BEWENSE devices is used not only to predict an obesity trend in a child but also to determine whether the child's BMI and weight are progressing within standard parameters for age and sex. Thus, the SVOPM, HOPM, ROPM, and EOPM modules also notify the child's parent through a local WTA 76 and child's health care provider through the WTA 16 of GOPS if the child is moving out of standard growth charts. In addition, the modules also are able to determine if there has been an abrupt change in the child's growth pattern (e.g., significant weight loss, gain, etc.). Also, all of the features of the previously mentioned embodiments are available in SVOPM, HOPM, ROPM, and EOPM for child's BMI monitoring.

In the Payable Entertainment Overweight and Obesity Preventing Module (PEOPM) a payable weight news sender WENSEPN 153 that is a modification of WENSE 151 may be used.

Figure 21:
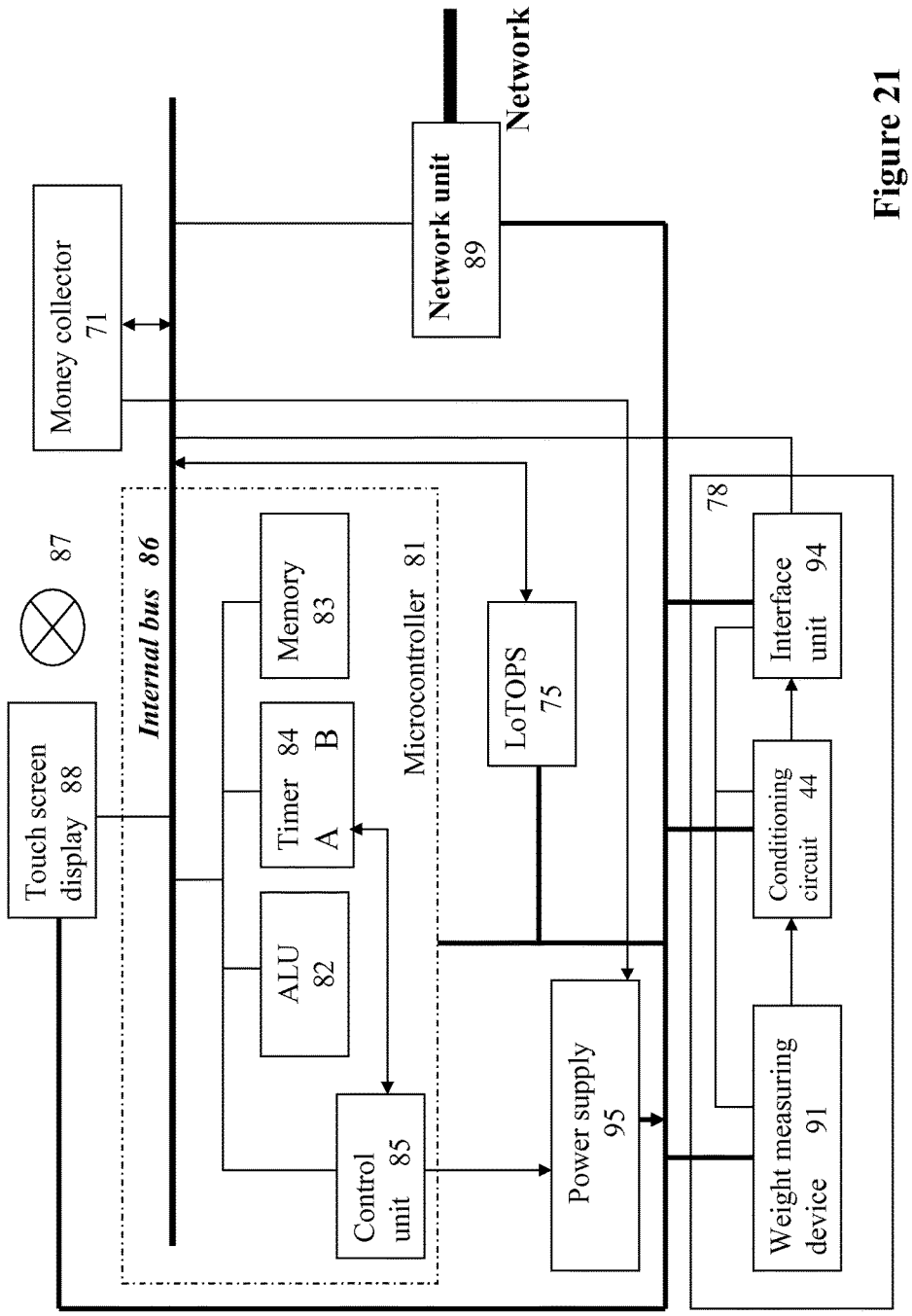
FIG. 21 is a structure of a Payable Weight News Sender WENSEPN.
Figure 22:
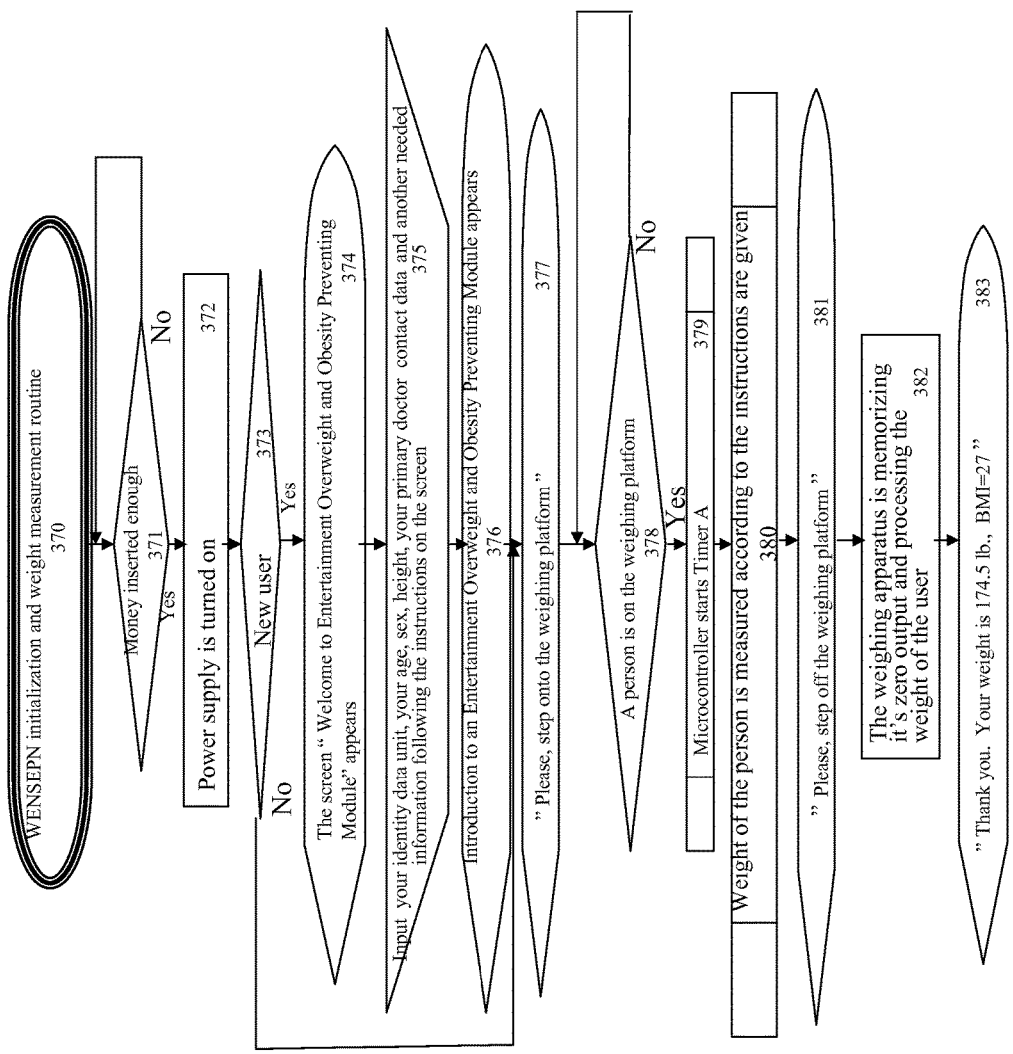
FIG. 22 is a flowchart for the Weight News Sender WENSEPN initialization and weight measurement routine or algorithm resident upon a microprocessor or memory of a module of an exemplary embodiment of the present invention.

FIG. 21 shows a block diagram of a WENSEPN 153 that is payable modification of a WENSE 151 that has a network service for transmitting the weight measurements collected by the WENSEPN 153 to the Trend Obesity Preventing Service (TOPS) 30. The WENSEPN 153 includes a microcontroller 81, a local Trend Obesity Preventing Service (LoTOPS) 75, a touch screen display 88, a weighing apparatus 78, a money collector 71, a network unit 89, a money collector-controlled power supply 95, and a light emitting diode 87. The following description is related to a touch screen type of a display-keyboard unit 88. Microcontroller 81, in turn, consists of an arithmetic-logic unit 82, a memory 83, a timer 84, a control unit 85, and an internal bus 86. The Local Trend Obesity Preventing Service (LoTOPS) 75 has the same structure as the LoTOPS 75 of WENSE 151. The weighing apparatus 78 consists of a weight measuring device 91, a conditioning circuit 44, and an interface unit 94 and has its own microcontroller and internal bus. The analog-to-digital converter is included into conditioning circuit 44. FIG. 22 shows a flowchart for WENSEPN 153 initialization and weight measurement routine 370, which is run when the module is powered up. Routine 370 is resident upon the microcontroller of the device. In step 371, the WENSEPN 153 checks to determine if money is inserted into the money collector by a user. If the money inserted by the person into the money collector equals or exceeds a predetermined threshold, the power supply 95 is turned on, in step 372. In step 373, a user is invited to input his/her identity data unit. The WENSEPN finds out if the user is new user. When the WENSEPN 153 is turned on by the user for the first time at decision node 373, a phrase "Welcome to Entertainment Overweight and Obesity Preventing Module" appears, in step 374. In step 375, the new user is invited to input his/her identity data unit, age, sex, height. The user is also asked to input his/her and a health care provider's contact information. After this initial sequence, the Introduction to an Entertainment Overweight and Obesity Preventing Module appears in step 376. When the WENSEPN 153 is not turned on for the first time at decision node 373, the process flows to step 377. In step 377, a user is invited to step onto a weighing platform of the weighing apparatus. In step 378, the WENSEPN 153 checks to determine if a person is on the weighing platform. If a person is not on the weighing platform, the microcontroller 81 continues to monitor a presence of a person on the weighing platform repeatedly. When a person is on the weighing platform, the process flows to step 379. In step 379, the microcontroller 81 starts the timer A that provides an output signal when 10 minutes have elapsed. Of course, one skilled in the art can recognize that other time ranges can be programmed into the unit. In step 380, the weight measuring device 91 weighs the person according to the instructions given. In step 381, screen "Please, step off the weighing platform" appears. The weighing apparatus checks its "zero" output and processes the weight of the person, in step 382, and shows this weight and BMI on the screen in step 383, and explanations about a person's measured BMI and recommended BMI are given.

After the required measurements of weight have been completed by WENSEPN 153, they are sent to the Local Trend Obesity Preventing Service (LoTOPS) 75 of the WENSEPN 153 through an internal bus. The LoTOPS 75 then determines if the person's BMI trends move towards an overweight or obesity condition. If the LoTOPS 75 discovers after acquiring a certain number of anthropology measurements that the person is becoming overweight or obese, the module sends a warning message to a person at the discretion of a person.

Once the measurements of weight have been completed, the WENSEPN 153 automatically sends the collected data to the TOPS service 30 through a data transmission medium such as a local network or Internet. After the information is received and analyzed by the TOPS service 30, an appropriate warning is issued at the discretion of a person to a person's healthcare professional if an overweight or obesity condition is forecast. If a resort or hotel does not have a data transmission medium such as a local network, the WENSEPN 153 directly sends the collected data to the TOPS 30 of the EOPM through the Internet. The TOPS of the EOPM may be located as a separate service TOPS 30 or may be included into entertainment processing center 250. For the users WENSEPN 153 who employs GOPS only several times and for a short period of time, WENSEPN 153 may show a fitness screen, weight graph, and any popular text. The recommendations about how to use WENSEPN in the future are given also. At this point, timer A finishes to count the assigned period of time, power supply 95 is turned off, and the screen of a touch screen display becomes dark. The money collector 71 will continue to have voltage supply.

Figure 23:
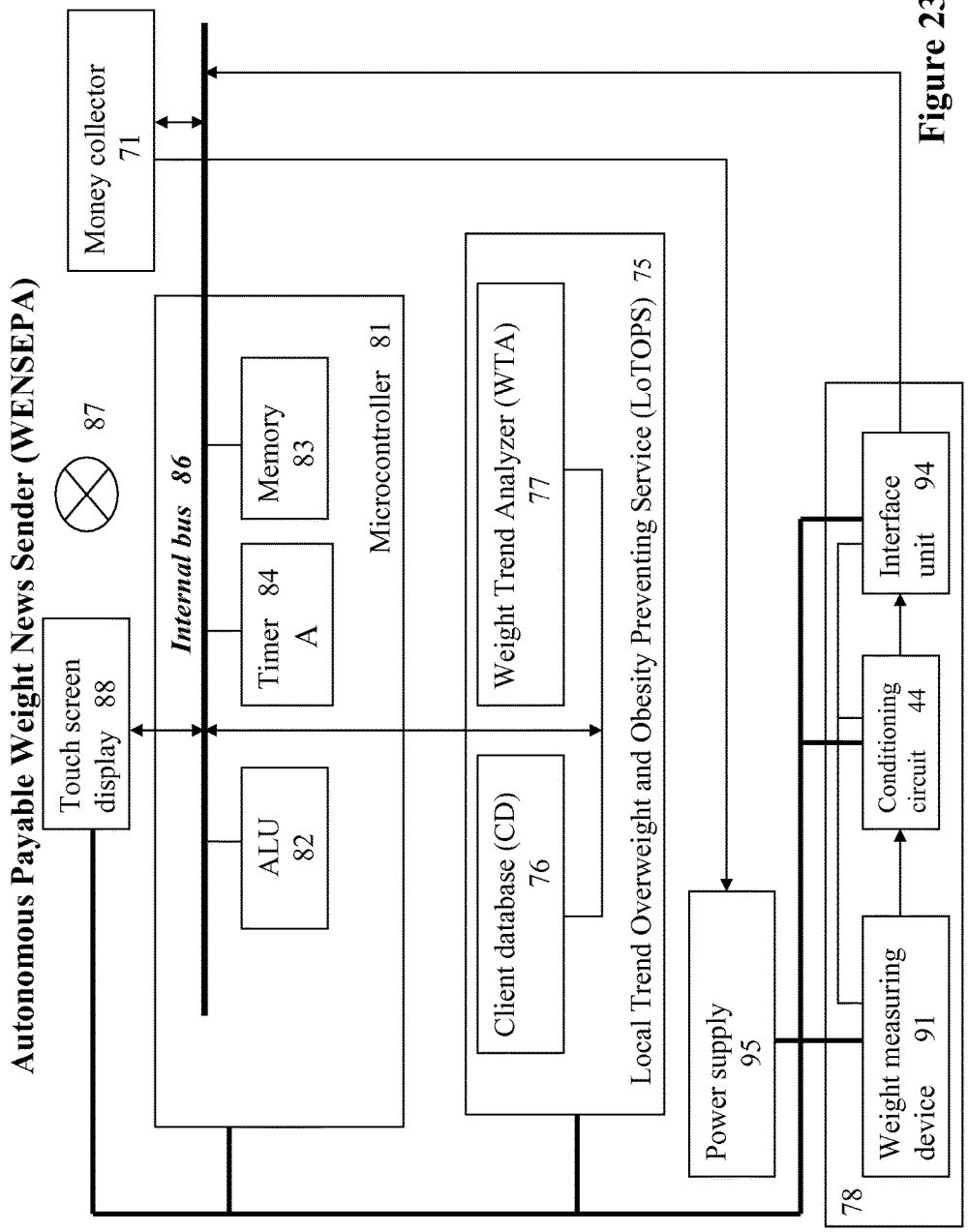
FIG. 23 is a structure of an autonomous Payable Weight News Sender (WENSEPA).

FIG. 23 shows a block diagram of a WENSEPA 155 that is payable modification of a WENSE 151 to serve in a payable PEOPM but does not have a network service for transmitting the weight measurements collected by the WENSEPA 155 to the Trend Obesity Preventing Service (TOPS) 30. Because of this, a local Trend Obesity Preventing Service (LoTOPS) 75 is included in WENSEPA 155. WENSEPA 155 includes a microcontroller 81, a LoTOPS 75, a touch screen display 88, a money collector 71, a money collector-controlled power supply 95, a light emitting diode 87, and a weighing apparatus 78. The following description is related to a touch screen type of a display-keyboard unit 88. Microcontroller 81, in turn, consists of an arithmetic-logic unit 82, a memory 83, a timer 84, and an internal bus 86. The weighing apparatus 78 consists of weight measuring device 91, a conditioning circuit 44, and an interface unit 94 and has its own microcontroller and internal bus. The analog-to-digital converter is included into the conditioning circuit 44. The LoTOPS 75 consists of a client database (CD) 76 and Weight Trend Analyzer (WTA) 77. The client database collects the name, age, sex, weight, height and other needed information of the person. The Weight Trend Analyzer (WTA) 77 has in its memory recommended weight for the individual depending on age, sex, and height of the individual. Analyzer 77 creates a graph of the person's BMI progress and compares it to a recommended one. If Weight Trend Analyzer 77 discovers that the person will be overweight or obese in the next several months the WENSEPA may show a warning message on the screen of touch screen display 88 to the user at his/her discretion only.

Some overweight and obese people are low and middle income people. They work very hard and are very exhausted, their lives are very stressful, and they don't have time enough to pay attention to their shape, weight, and health.

This Global Overweight and Obesity Preventing and tracking System is very convenient for use at home, in any educational institution, school, company, medical facility, community centers, etc., which may make it easier for people to use especially people who work very hard and are exhausted and do not have time enough to pay attention to their shape, weight, and health.

This system is very low time consumed (several seconds) and serves well for users in the most convenient places for quick collecting (without pushing any push buttons) of the weight measurements of the individual when one engages (sits down in a car seat, steps onto a scale next to a his/her bed or just lies upon the bed) a weighing platform. The system automatically collects measurements and forecasts a possible overweight or obesity condition of the individual that may happen in a short period of time that is sufficient to prevent future overweight or obesity condition. There is evidence that thanks to the early intervention even slight adjustments to the person's lifestyle may be sufficient to prevent development of the obesity. The system automatically analyzes the dynamics of the weight changes. It predicts the overweight or obesity trend within the short term that is sufficient to address the issue. When an overweight tendency is detected the supervising physician is electronically notified. This warning will trigger a pre-overweight or obesity treatment. It is clear that effectiveness of treatment is much higher and cost of treatment is much less if one starts to solve the problem of obesity before any serious mental and body changes take place. Because the system is low-cost, it may be used in the areas with vulnerable populations without any surveys and medical check-ups.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An obesity predicting system, the system comprising:
a plurality of modules each of the plurality of modules having a computer having stored instructions that when executed causes the computer to collect anthropometry measurements of an individual from a variety of locations and predict an obesity condition based upon collected anthropometry measurements of the individual, wherein the plurality of modules comprise:
at least one on-board vehicle overweight and obesity predicting module configured to collect anthropometry measurements of an individual in a vehicle;
at least one in-building overweight and obesity predicting module configured to collect anthropometry measurements of an individual at a fixed location; and
at least one entertainment overweight and obesity predicting module configured to collect anthropometry measurements of an individual at an entertainment facility; and
a communications network for linking the at least one on-board vehicle overweight and obesity predicting module, the at least one in-building overweight and obesity predicting module, and the at least one entertainment overweight and obesity predicting module to a computer of the obesity predicting system, the computer of the obesity predicting system having stored instructions that when executed causes the computer of the obesity predicting system to collect the anthropometry measurements from each of the plurality of modules and use the collected anthropometry measurements to predict whether the individual is trending towards an obesity condition, wherein the computer of the obesity predicting system uses a currently collected weight measurement to calculate a BMI progress based in part upon an age of the individual and then determine if the individual is trending towards an overweight condition based the comparison of the calculated BMI progress with a recommended BMI progress, wherein the system after determining on more than one occasion that the individual is trending towards the overweight condition, the system will request authorization to send a warning message to a health care provider of the individual, upon receipt of authorization to send a warning message to the health care provider of the individual, the system will send the warning message to the health care provider of the individual, and wherein the system is configured to determine whether a different individual is having their weight measured by the system by determining whether two consecutive measurements of the individual are greater than a predetermined amount.

2. The system as in claim 1, wherein the stored instructions of the at least one in-building overweight and obesity predicting module when executed causes the at least one in-building overweight and obesity predicting module to store and analyze height, age, gender and weight information of the individual at the fixed location.

3. The system as in claim 2, wherein the stored instructions of the at least one in-building overweight and obesity predicting module when executed causes the at least one in-building overweight and obesity predicting module to collect measurements of weight and height of the individual and wherein the obesity predicting system predicts the obesity condition by using a body mass index.

4. The system as in claim 3, wherein the stored instructions of the at least one in-building overweight and obesity predicting module further comprises a device for obtaining the height of the individual and wherein the system is configured to determine whether a prescribed period of time has elapsed since the height of the individual has been measured.

5. The system as in claim 2, wherein the stored instructions of the plurality of modules when executed causes the plurality of modules to perform the following functions when the individual steps onto a weight and height measuring platform: determine the individual's identity; measure the individual's weight and height; provide audio communication with the individual; provide results of measurements in the form of weight, height, body mass index and transmit the results of the measurements to the computer of the obesity predicting system; forecast obesity of the individual in a predetermined period of time; and provide an alert to the individual when the forecast of obesity in the predetermined period of time has been determined.

6. The system as in claim 1, wherein the computer of the obesity predicting system further comprises a client data base and additional stored instructions that when executed send a warning to the individual's health care provider when the system determines that the obesity condition will develop in a predetermined period of time.

7. The system as in claim 1, wherein the anthropometry measurements include weight and height of the individual and wherein the obesity predicting system is configured to provide a warning to the individual if the obesity condition will occur in a predetermined time period.

8. The system as in claim 7, wherein the at least one on-board vehicle overweight and obesity predicting module further comprises a switch inserted in a back of a seat of the vehicle, wherein the switch will provide a signal to the computer of the at least one on-board vehicle overweight if the individual's back is touching the seat.

9. The system as in claim 1, wherein the at least one in-building overweight and obesity predicting module further comprises an apparatus measuring the individual's height and weight while they are lying on a bed.

\* \* \* \* \*